(12) United States Patent  
Jensen et al.

(10) Patent No.: US 9,358,048 B2
(45) Date of Patent: Jun. 7, 2016

(54) FUSION IMPLANT FOR FACET JOINTS

(75) Inventors: Harm-Iven Jensen, Noer (DE); Helmut D. Link, Hamburg (DE)

(73) Assignee: Facet-Link Inc., Rockaway, NJ (US)

( * ) Notice: Subject to any disclaimer, the term of this patent is extended or adjusted under 35 U.S.C. 154(b) by 0 days.

(21) Appl. No.: 13/309,147

(22) Filed: Dec. 1, 2011

(65) Prior Publication Data

US 2012/0143337 A1 Jun. 7, 2012

Related U.S. Application Data

(60) Provisional application No. 61/418,487, filed on Dec. 1, 2010.

(30) Foreign Application Priority Data

Dec. 1, 2010 (EP) .................................... 10193333

(51) Int. Cl.
*A61B 17/70* (2006.01)

(52) U.S. Cl.
CPC .................................. *A61B 17/7064* (2013.01)

(58) Field of Classification Search
CPC .............. A61F 2/4405; A61B 17/7064; A61B 17/7071; A61B 17/7047; A61B 17/7025; A61B 17/7052
USPC ........................................ 606/247, 250–253
See application file for complete search history.

(56) References Cited

U.S. PATENT DOCUMENTS

| | | | |
|---|---|---|---|
| 6,358,254 B1 * | 3/2002 | Anderson | 606/103 |
| 7,083,650 B2 * | 8/2006 | Moskowitz et al. | 623/17.11 |
| 2005/0143818 A1 * | 6/2005 | Yuan et al. | 623/17.11 |
| 2006/0036324 A1 | 2/2006 | Sachs et al. | |
| 2006/0265074 A1 * | 11/2006 | Krishna et al. | 623/17.15 |
| 2008/0249568 A1 * | 10/2008 | Kuiper et al. | 606/247 |
| 2009/0012566 A1 * | 1/2009 | Fauth | 606/247 |
| 2009/0024169 A1 * | 1/2009 | Triplett et al. | 606/248 |
| 2009/0029169 A1 * | 1/2009 | Takamoto et al. | 428/402 |
| 2010/0076493 A1 * | 3/2010 | Fauth et al. | 606/279 |

FOREIGN PATENT DOCUMENTS

WO WO2009094629 7/2009
WO WO2010122472 10/2010

OTHER PUBLICATIONS

European Search Report dated May 26, 2011 in related EP Application No. 10193333.1 in German, 8 pages.

* cited by examiner

*Primary Examiner* — Jan Christopher Merene
*Assistant Examiner* — Atiya Mahmud
(74) *Attorney, Agent, or Firm* — Morrison & Foerster LLP

(57) ABSTRACT

A fusion implant for a facet joint comprises a bearing module and a fusion module, in which the fusion model is arranged on the bearing module and has a holder for a transfacetal fastener, whereby the bearing module includes an expansion element and jaw elements, which have contact surfaces for the lamina on their outer sides moving away from each other and which are arranged to move longitudinally on a guide, so that the distance of the fusion module is changeable using the expansion element. The bearing module forms a secure and safe anchoring for the fusion module, which can be repositioned. In addition, the bearing module has the effect of an augmentation, and as a result treatment is possible even on vertabrae that are weakened by defects.

40 Claims, 25 Drawing Sheets

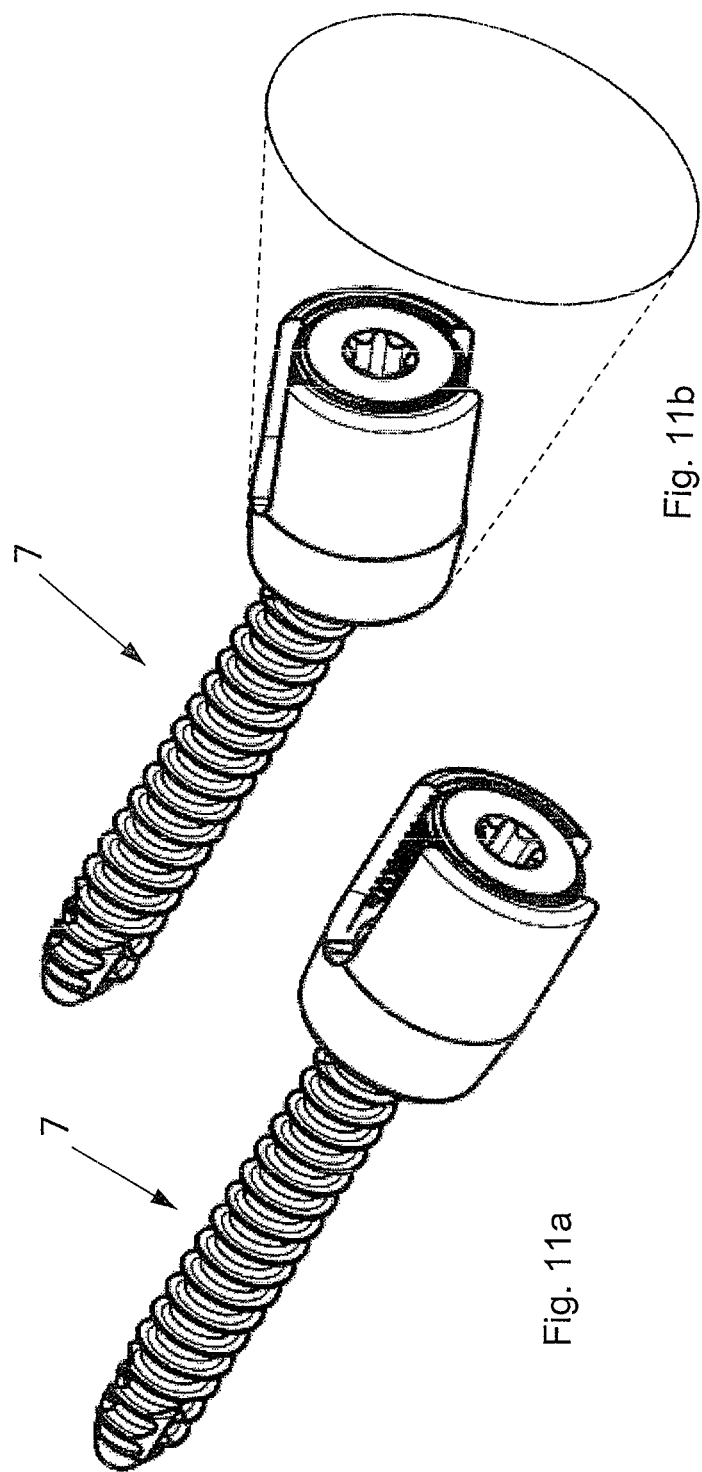

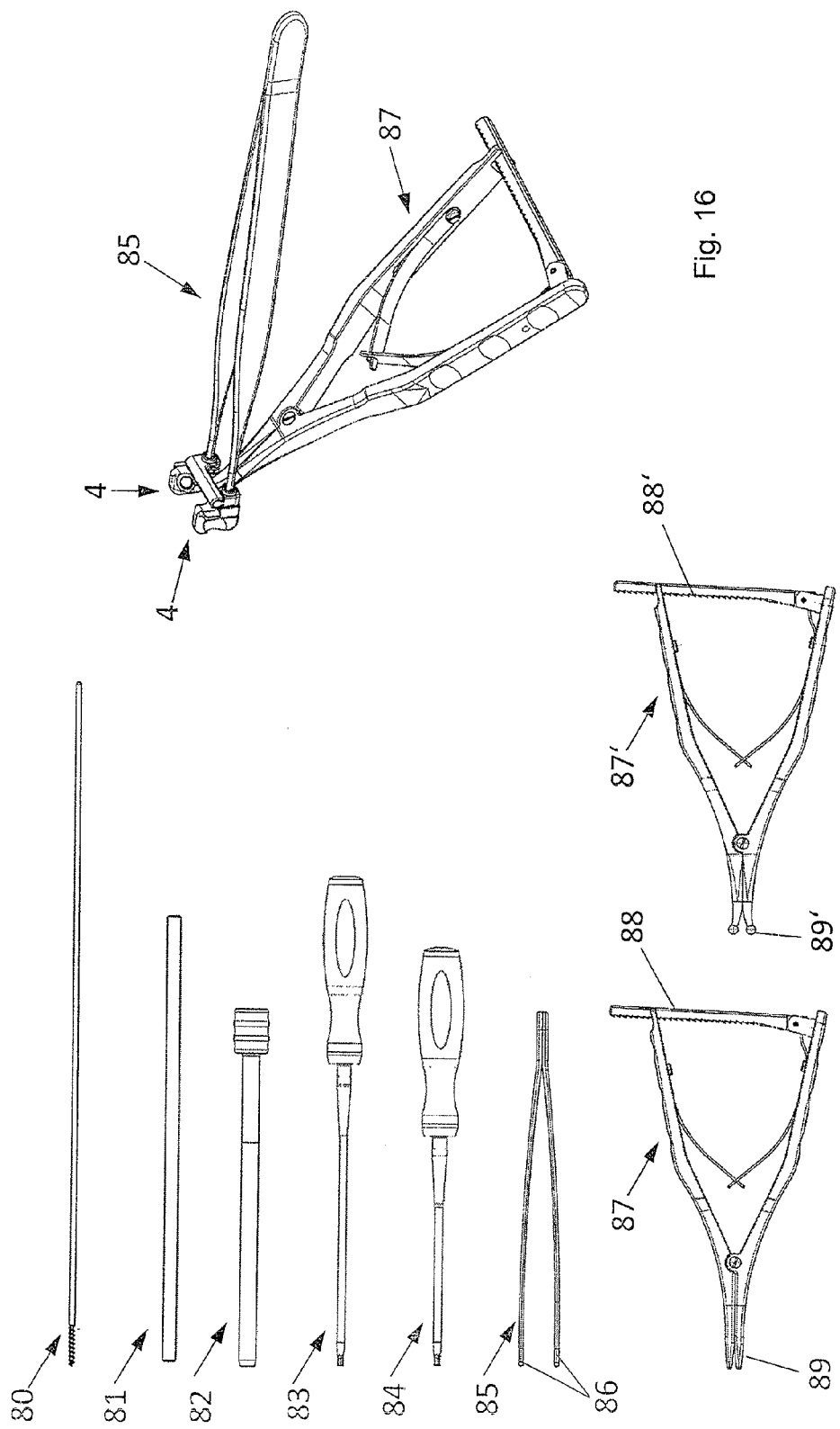

US 9,358,048 B2

FUSION IMPLANT FOR FACET JOINTS

REFERENCE TO RELATED APPLICATIONS

This application claims the benefit of U.S. Provisional Application No. 61/418,487, filed Dec. 1, 2010, the entire contents of which are incorporated herein by reference. This application also claims the priority of European Patent Application No. 10193333.1, filed Dec. 1, 2010, the entire contents of which are incorporated herein by reference.

FIELD OF THE INVENTION

The invention relates to a fusion implant for facet joints, comprising a fusion module for connecting the facet joints of neighboring vertebrae and a support module holding the fusion module.

BACKGROUND OF THE INVENTION

The spinal cord is a central structural element of the human skeleton comprising a plurality of vertebrae, which are arranged one above one another for the transfer of loads and are connected to one another with articulation to allow movements. The vertebrae of the spinal cord are not identical but instead differ in shape depending on their arrangement on the spinal cord. However, they have a few things in common. For example, each vertebra has a solid vertebral body with two osseous protrusions (pedicles) protruding laterally and to the rear, each in turn being connected in its rear portion via a bony arch. In the connecting area this bony arch is designed as a broad plate (lamina) and has a spinal protrusion extending to the rear at the center. The spinal protrusion (spinal process) as well as two additional transverse protrusions on the lateral surfaces of the pedicle form attachment points for muscles and ligaments. In the area where the pedicles develop into the broad lamina, one upper joint protrusion and one lower joint protrusion are arranged on each side of the vertebrae. They each form part of a facet joint having a neighboring lower or upper vertebra. In addition, it is provided that for transfer of load on the vertebrae, an intervertebral disc is arranged between the vertebral bodies of neighboring vertebrae, filling up the interspace between the relatively flat cover surfaces of neighboring vertebral bodies. The region bordered by the back sides of the vertebral body and the bony arch (vertebral arch) forms a cavity in which nerve fibers running parallel to the spinal cord are accommodated.

Back pain or back ache often occurs due to degeneration of the spinal cord. One of the main causes for back pain is the interaction between two neighboring vertebrae. This relates in particular to intervertebral discs as one of the main causes, but also in a substantial number of cases the pathology also involves at least the facet joints. Because of wear or disease, the articulated connection of two neighboring vertebrae created for the facet joints may be damaged. This may lead to restricted movement, pain or even loss of mobility. Various approaches have become known for treatment. In particular a definite improvement can be achieved by stabilizing the facet joint. In many fields, this is done by immobilizing the facet joint by a fixed connection. We speak here of fusion of the facet joint.

WO 2009/094629 A1 has disclosed a fusion implant comprising long bone screws which are screwed through both of the facets forming a facet joint. This screw is designed as a compression screw, tightening the cooperating halves of the facet joints so that the joint is immobilized. To be able to transfer the required forces to the vertebral body, the screw head is provided with a separate supporting sleeve arranged in a pivotably mobile manner. With its pivotable mobility, the transfacetal compression screw may assume various angular positions to the supporting plane determined by the supporting sleeve. We speak here of a polyaxial arrangement of the transfacetal screw. A separate screw is provided for each of the two facet joints of a vertebral body (on the left side or on the right side). The known fusion implant offers the advantage of relatively simple implantability because it has small dimensions and therefore can be implanted even in minimally invasive surgery. However, this known fusion implant requires a relatively strong and intact bone structure on the vertebral body, in particular in the area of the supporting surface of the pivotably movable collar around the screw head.

US 2005/0192572 A discloses a fusion implant which also provides polyaxially guided transfacetal facet screws for fusion of the two joint halves of a facet joint. In contrast with the implantation arrangement described previously, this embodiment additionally has a traverse piece on which the two transfacetal fusion screws (for the right and left facet joints of a vertebral body) are guided via sliding connectors. The sliding connectors are designed so that they are fixed in their position by clamping forces which occur on insertion and tightening of the facet screw. The advantage of this implantation arrangement is that a stable positioning of the one facet screw in relation to the facet screw on the other side of the vertebral body is achieved. However, there is no control of the absolute position of the fusion screws with respect to the vertebral body. Furthermore, this implantation arrangement also requires a relatively strong and intact bone structure of the vertebral body.

SUMMARY OF THE INVENTION

An object of the present invention is to create an improved fusion implant of the type defined in the introduction which avoids the disadvantages mentioned above.

This can be achieved by the features as broadly disclosed herein. Advantageous further embodiments are the subject matter of the detailed embodiments described below.

According to the invention, it is provided that in the case of a fusion implant for a facet joint comprising a support module and a fusion module, where the fusion module is arranged on the support module and has a holder for transfacetal fastening means, the support module comprises an expansion element and jaw elements which have contact surfaces for the lamina on outsides facing away from one another and are arranged longitudinally displaceably on a guide so that the spacing of the fusion modules is variable by means of the expansion element.

The invention is based on the idea of creating a fusion implant with which the function of holding and positioning on the vertebral body is uncoupled from the function of the actual action on the facet joint. With the support module a secure and precise positionable anchoring of the fusion implant on a vertebral body, in particular on laminar sectional surfaces, is achieved. A solid and secure platform is created so that the components creating the fusion can be positioned accurately and reliably in absolute terms based on the vertebral body and also in relation to one another. Furthermore, the modular design offers the advantage that it is especially well suited for implantation by means of minimally invasive surgery.

Furthermore, an augmentation is achieved with the support module so that the inventive fusion implant is suitable in particular for use on vertebral bodies also those having larger defects, in particular in the area of the lamina. The invention thus offers the great advantage that it can even be employed with the vertebral body is weakened due to previous decompression therapy. Especially in the case of this therapy, which occurs very commonly in practice, a facet joint fusion had previously been contraindicated. The invention now makes this possible and thus greatly increases the number of patients who can be helped.

The invention thus combines advantages with regard to broad applicability thanks to augmentation even in the case of vertebral bodies having substantial defects and more precise positioning on the vertebral body with a procedure that is conservative for patients, thanks to the minimally invasive implantation. Facet fusion as the "gold standard" can thus be combined with other therapeutic techniques.

First, a few of the terms used shall be explained:

The term "transfacetal" is understood to refer to a transverse crossing of the facet joint. The facet joint here comprises a lower facet of the vertebra on which the inventive implant is to be positioned and an upper facet of the underlying vertebra, together forming the facet joint.

The term "cephalad" is understood to refer to a direction pointing upward, based on the implanted position, i.e., toward the head of the patient. Accordingly, the term "caudal" is understood to refer to the opposite direction, i.e., pointing from the head downward.

The fusion module preferably has a main bearing on an upper facet and a counterbearing on a lower facet of the facet joint to be fused. The fusion forces can thus be in a defined manner which is ultimately protective of bone substance. The counterbearing may be arranged as a separate element on the respective facet, or it may be designed in one piece with the element producing the actual fusion, for example, as a bone thread of a transfacetal screw as a fastening element. The transfacetal screw may be designed to be cannulated or solid.

The main bearing is preferably pivotable. Thus the direction in which the facet fusion takes place and thus also the function axis may be altered. Such a polyaxial bearing allows an improved adaptation to individual anatomical conditions. An adjustment range of +I–15 degrees in all directions has proven successful. In an expedient embodiment, the main bearing comprises a spherical cup-shaped receptacle seat in which a fixation sleeve is pivotably supported. Due to the spherical interface between the fixation sleeve and the receptacle seat, rotational degrees of freedom in all directions are obtained. This design is especially favorable when a transfacetal screw is provided for fusion.

For reasons of increased fastening reliability, the fusion module is usually rigidly arranged on the support module. However, the possibility of it being arrangement flexibly on the support module should not be ruled out. This may offer advantages with regard to compatibility with dynamic movements of the spinal cord.

The contact surface of the jaw elements may be shaped in such a way that it is narrower in the cephalad region. Thus the thickness of the implant may be reduced in a critical area where an unwanted pressure could otherwise easily be exerted on nerve fibers running in the spinal cord or on tissue surrounding them. This increases the tolerability of the implant. The fusion module is advantageously arranged in the caudal region of the contact surfaces where enough room is available for the implant without creating an increased risk of irritation of surrounding tissue.

In many cases with a vertebra on which the inventive fusion implant is to be arranged, the lamina is completely removed because of a decompression treatment. The resection surfaces of the lamina are joined together via the support module inserted into the clearance so that functionally the arch is closed again. However, it may also be the case that complete resection of the lamina over its full height is not necessary but instead it remains in existence over a portion of its height. This remainder alone is no longer completely fully load-bearing mechanically. This is where the present invention begins with a variant of the fusion implant, which has a small structural height. The support module of the fusion implant, which is provided for embedding in the lamina, therefore has a smaller dimension in the cephalad-caudal direction, which is preferably less than half the extent of the contact surface in this direction. The fusion implant is thus so compact that it can be placed beneath the remainder of the lamina and can reinforce it, while at the same time forming a solid basis for the fusion of the facet joints. The fusion module is preferably arranged in the central area of the jaw elements, and the jaw elements are interchangeable. Thus the relationship between the jaw elements and their guidance can be inverted. If the guidance with the jaw elements in the basic version forms a U-shaped structure that is open at the bottom or an H-shaped structure, then thanks to the interchangeability of the jaw elements the inversion results in a U-shape that is open at the top. This is suitable in particular for implantation beneath a resection residue of the lamina with the spinal protrusion.

In addition, for greater increase in compactness, the fusion module is not arranged on the support module, or at least is so arranged on one of the jaw elements, preferably on the jaw elements on the support module side. It should be noted that the support module can be provided both one-sided, meaning on one jaw element only, or two-sided, meaning on both jaw elements.

The support module with its guide in particular is preferably coordinated with the fusion module so that a coaxial access route to the transfacetal screw in the fusion module is free. In other words, there is unhindered access to the head of the transfacetal screw in the direction of the lengthened screw axis. Thus the structural prerequisites for being able to tighten the transfacetal screw in the installed state at the implantation site are created.

In one embodiment, a pedicle support is arranged on the support module. This particularly advantageous embodiment deserves independent protection even without the fusion module. The pedicle support allows a secure and robust fixation, but it also makes high demands of the positioning accuracy. Thanks to the inventive arrangement on the support module, accurate positioning is achieved so that the risk of improper positioning that exists in the state of the art and can result in substantial damage is eliminated. This is the case in particular when a bearing for pedicle screws is provided on the pedicle support. To nevertheless allow an adequate adjustment option for adaptation to the individual anatomy of a patient, the pedicle screw is preferably polyaxially supported. To do so, this bearing is designed according to that of the transfacetal screw.

The pedicle support is advantageously held on an alignment device of the support module. At this point the pedicle support may be added or omitted in modular form. A unilateral arrangement of the pedicle support is also readily possible in this way.

In another preferred embodiment, which provides independent protection if applicable, the pedicle support is arranged on the jaw element. This permits a more compact form of the support module, and as a result a pedicle support can also be arranged in very narrow spatial conditions. Moreover, the flow of weight is reduced over which the holding strength is transferred into the vertebrae that have received the fusion implant. This results not only in a more compact construction, but also in a more rigid one. The pedicle support is fastened preferentially with a pivot bearing. In this way an adjustment to the anatomical conditions of the particular vertebrae can be made. The fusion implant in this way is not only made more useful on many sides, but also very compact. It can be used in narrow anatomical conditions.

The pivot bearing intentionally has a slotted spherical cap bearing body. In this way a reliable and compact placement can be shaped in the form of a spherical receptacle, which can be made in the shape of an eye at the end of a pedicle support. The slotting combines good assembly ability and adjustability with secure fixation. The spherical cap bearing body is provided with a pass-through opening for a setting screw, whereby the pass-through opening has a circular ring collar on its edge. In this way a secure positioning of the bearing body in its normal location is made possible. Furthermore, the pass-through opening can be provided with a preferentially short counter-thread with a radial member facing inward. "Short" means up to 2 revolutions. In this way a stronger fixation and clamping effect can be achieved, and as a result the pedicle support is even more secure in its position.

Preferentially, the acceptance point in the pedicle support has several sections, of which one is shaped as a conical pass-through borehole and the other as a thread section.

In an expedient embodiment, the pedicle support is designed so that the pedicle screws have parallel axes which lie approximately across the direction of adjustment of the guide. This permits a compact embodiment of the pedicle support. It preferably has a dimension such that its lateral dimensions amount to no more than 1.5 times the lateral dimension of the support module. Alternatively the pedicle support may also be provided so that it extends laterally, protruding definitely farther laterally. The axes of the pedicle screw here are aligned so they converge toward the center of the support module. This allows an especially stable fastening means.

The present invention achieves fastening security through elastic widening of the lamina and/or the vertebral arch. For this purpose, the support module has an expansion element, which preferably includes a guide made of a rod moving lengthwise in a groove. With this guide, the expansion element and with it the jaw elements can be spread so wide that the resectioned area of the lamina can be bridged over. Preferentially the rod and the groove are safely screwed together with a form-shaped gripping member. In order to avoid overexpansion, the rod is expediently made thicker on its free end. This cannot enter into the groove, and thus prevents a move outwards due to overexpansion. The thickened part can be made in one piece with the rod, but preferentially it should be made as a screw to be set in by its free end into the front face.

In combination with the externally positioned supporting surfaces of the jaw elements, the expansion element has the advantage that collapse of the vertebral arch, which could in the past occur in an unwanted manner, is rendered impossible. On the contrary, under a pressure which would previously have led to collapse, the reinforcing implant is only pressed more securely into its seat and thus can fulfill its function. Although the elastic widening per se can ensure a seating with long-term stability, a slip lock for the jaw elements may additionally be provided to thereby further increase the long-term fastening security.

The slip lock is advantageously designed as an alignment device acting between the jaw elements and the guide. After expanding easily, the expansion position thereby achieved is easily secured with such a method of clamping. This prevents slipping of the jaw elements. If the requirements of safety with respect to unwanted movements of the jaw elements are higher, the slip lock may be provided with catch elements which are arranged between the jaw elements and the guide. Expediently the catch elements comprise a fluting and catch protrusions engaging in the grooves. With such a catch engagement as that achieved by the fluting in combination with the catch protrusion, the result is a form-fitting means of securing. This offers the advantage that sufficiently secure holding of the reinforcing implant can be achieved even in very active patients with appropriate load on the spinal cord.

Preferably at least one of the jaw elements is provided with an alignment device. Thus the orientation may be varied from its outside surface to the guide. This allows a finer adaptation of the fusion implant to the actual anatomical conditions after the laminectomy.

An embodiment of a bearing of the alignment device as a locking screw has proven especially successful. In the unstressed state, this allows rotation about its central axis whereas it secures the orientation achieved in the stressed state. The other jaw element is expediently equipped accordingly.

It has proven successful to provide the alignment device with a twist-preventing device, which is designed to limit the angle that may be assumed by the jaw elements in relation to the expansion elements. A limit to an adjustment range of max. 45 degrees, preferably max. 30 degrees has proven advantageous.

The stop surfaces on the jaw elements preferably have protruding spikes. Tried and tested forms for such spikes include, for example, conical tips, pyramids, prismatic or V-shaped elevations. Thus a secure primary fixation can be achieved. To additionally achieve a rapid and secure secondary fixation, the contact surfaces are preferably provided with a coating that promotes bone growth. This may be in particular hydroxyapatite or other osteoinductive substances.

The contact surfaces are preferably arranged on both of the jaw elements in such a way that they are flush with one another. This is understood to mean that they have neither a horizontal nor a vertical offset as seen in the direction of the vertical pathway of the expansion element. Thus an asymmetrical action of force on the fusion element is prevented so that no unwanted torque acts on the fusion implant, tending to rotate it out of its intended position.

The subject matter of the present invention, which provides independent protection in a particular case, is also a set comprising an implant as described above and instruments including an elongated guide wire, a guide shaft through which the guide wire can be inserted, having one end designed for being held on the main bearing of the fusion module and a cannulated screwdriver. After partial or complete resection of the lamina, the implant is inserted into the clearance thereby created. Optional setting pincettes may be provided for this purpose. In the next step, the expansion element of the implant is spread by means of optional spreading tongues which may be attached at the same time as the setting pincettes thanks to their angling in a special embodiment. It should be pointed out that the spreading forceps may be designed together with the setting pincettes as a combined instrument. Then the guide wire is advanced through the guide shaft, namely through the main bearing, first into the upper facet and then further into the lower facet. Thus the implantation path for the transfacetal screw is defined. Next the guide shaft is removed and a tissue-protective tube is pushed onto it. Its inside diameter is designed to be so large that the transfacetal screw can be guided through it. The transfacetal screw is cannulated, i.e., it has a through-opening along its central axis and may thus be pushed onto the guide wire and guided on it through the tissue-protective tube to the fusion module. The transfacetal screw is tightened securely by means of a screwdriver which is also cannulated and is placed on the guide wire in the same manner. Thanks to the guide wire, the position here is controlled. Once the screw has been tightened, the position is fixed and the guide wire together with the tissue-protective tube can be removed. After the transfacetal screw has been attached on the other side in the same way, the spreading forceps may be removed. It should be pointed out that solid transfacetal screws may also be used, but then they are not guided through the guide wire on insertion. In conclusion, the locking screws can be tightened and the expansion element of the fusion implant is then secured. The implant is thus inserted.

The present invention also extends to a method for implantation which is performed with the aforementioned steps. It is suitable in particular for implantation with a less invasive dorsal access ("limited invasive dorsal approach").

BRIEF DESCRIPTION OF THE DRAWINGS

The invention will now be explained below with reference to the accompanying drawings on the basis of advantageous exemplary embodiments, which show:

FIGS. 11a, b show detailed views of the setting screws of the fourth exemplary embodiment shown in FIG. 10;

FIG. 15 shows instruments for implantation in implants according to the exemplary embodiments;

FIG. 16 shows an application example for instruments from the instrument set;

DETAILED DESCRIPTION OF THE INVENTION

Figure 1A:
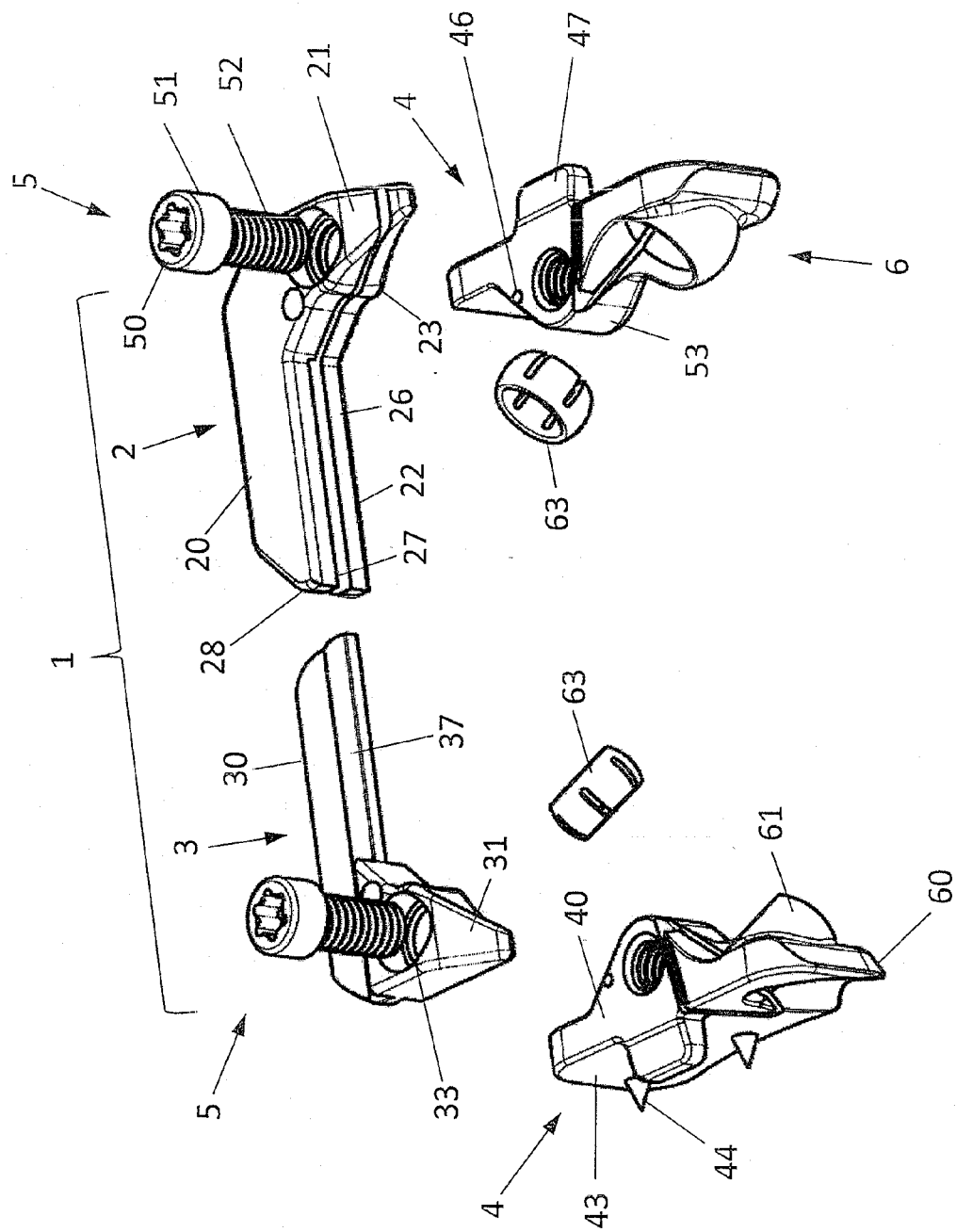
FIGS. 1a, b show a perspective view of a first exemplary embodiment in an assembled state and a disassembled state.

A first exemplary embodiment of an inventive fusion implant comprises in its totality a support module labeled with reference numeral 1 and a fusion module 6. The support module 1 is designed in the bridge style. It comprises a rail body 2 in which a slide 3 is guided so it is longitudinally displaceable. A jaw element is arranged on the rail body 2 and on the slide 3. It has a contact surface 43 on the lamina of a vertebra on its sides facing outward, i.e., away from one another.

The rail body 2 and the slide 3 cooperate in such a way that in the longitudinal displacement the distance between the jaw elements 4 changes. The rail body 2 and the slide 3 therefore cooperate in the manner of an expansion element, which can adjust the distance between the two outside surfaces 43 of the two jaw elements 4 to be of different sizes. Depending on the adjustment of the expansion element, i.e., the relative positioning between the rail body 2 and the slide 3, which is guided thereon in a longitudinally displaceable manner, a support module 1 may be created, bridging interspaces of different widths formed by resection in the lamina 93 of a vertebral body.

The rail body 2 has a supporting web 20 on whose one end (at the right in FIG. 1) a holder 21 is designed. The web 20 has a rectangular cross section and has two lateral sides 24, 25. A guide groove 28 in the web 20 having a circular design in the exemplary embodiment shown here is arranged parallel to the lateral sides 24, 25. It is connected by a slot 27 to the lateral side 24 of the web 20, such that the slot 27 extends into the holder 21. The transitional area between the lateral side 25 of the web 20 and the holder 21 on said end of the web 20 may be provided with a chamfer.

The slide 3 has as the main components a guide rod 30 and a holder 31, which is designed to be symmetrical with the holder 21 of the rail body 2 with regard to its external shape. The guide rod 30 has a shape that is complementary to the groove 28 of the rail body 2, thus forming a longitudinally displaceable guide. In the exemplary embodiment shown here, the guide rod 30 is provided with a circular cross section because of the circular shape of the guide groove 28. To achieve twist-proof securing means, a narrow guide strip 37 is designed on the side of the guide rod 30 facing the holder 31. The dimensions of this guide stripe are selected so that it is narrower than the width of the slot 27 on the rail body 2 in a relaxed state but at least as great as the width in a stressed state, as explained in greater detail below. The slide 3 is thus longitudinally displaceable but is guided on the rail body 2 in a rotationally secured manner.

The holders 21, 31 on the rail body 2 and/or the slide 3 are essentially designed symmetrically. Therefore they are explained jointly below. The holders 21, 31 each comprise a through-opening 23 and/or 33, the axis of which is oriented perpendicularly to the axis of the longitudinally displaceable movement between the rail body 2 and the slide 3. The through-openings 23, 33 serve to position and secure one each of the jaw elements 4 of an alignment device 5.

The jaw elements 4 are also designed symmetrically with one another. On their contact surface 43 facing away from the other jaw element 4, respectively, they each have a plurality of spikes 44 for anchoring in lateral cut surfaces 94 of the lamina 93 of the vertebra 9 (see FIG. 13). The contact surfaces 43 with the spikes 44 are preferably provided with a coating such as calcium phosphate or hydroxyapatite to promote bone growth. A protrusion 47 extending outward is arranged at the transition of the contact surfaces 43 with the top side of the jaw elements 4. It functions as a depth stop and limits the depth of insertion of the jaw elements 4 and thus the entire implant on the lamina 93. This prevents the jaw elements from being inadvertently inserted too far, which could cause irritation or injuries of tissue or nerve fibers in the medullary canal. In addition, a catch protrusion 46 is provided on the top side of each of the jaw elements 4. It is designed to cooperate with fluting 26 arranged on the underside 22 of the web 20.

This should achieve the effect that in the installed state, the jaw elements 4 are secured against inadvertent twisting or displacement in the case of the jaw element 4 with respect to the web 20. The catch protrusion 46 cooperating with the fluting 26 forms a catch engagement, which secures the position of the jaw elements 4 in a form-fitting manner, thereby preventing and unintended misalignment, even under high loads.

For locking the position of the jaw elements 4 with respect to the web 20, alignment devices 5 are provided on the holders 21, 31. Each has a locking screw designated as a whole with reference numeral 51, having a screw head 51 and a shaft 52 with an outside thread. The head 51 has a larger diameter than the through-opening 23, 33 in the holder 21 and/or 31, so that the shaft 52 can engage in the jaw element 4 through them in a corresponding mating thread. By tightening the locking screw 50, the jaw element 4 is thus pulled against the underside of the expansion element formed by the rail body 2 and the slide 3, so that the expanded position of the jaw elements is secured with regard to their relative distance from one another and also in the relative positioning (also with respect to the web 20) in both a form-fitting and friction-locked manner.

Under the influence of the aligning device 5, the slot 27 in the rail body 2 is also compressed, namely to such an extent that it clamps the guide strip 37. This further secures the slide 3 with respect to an unwanted longitudinal displacement in relation to the rail body 2.

The contact surfaces 43 of the jaw elements 4 extend longitudinally essentially in a direction parallel to the outside surfaces of the holders 21, 31. The depth of the elements 4 is nevertheless designed to be thinner at a cephalad end closer to the web than on the caudal end, which is opposite therefrom and also remote from the web. A fusion module 6, which is described in greater detail below, is also arranged on this.

Figure 14:
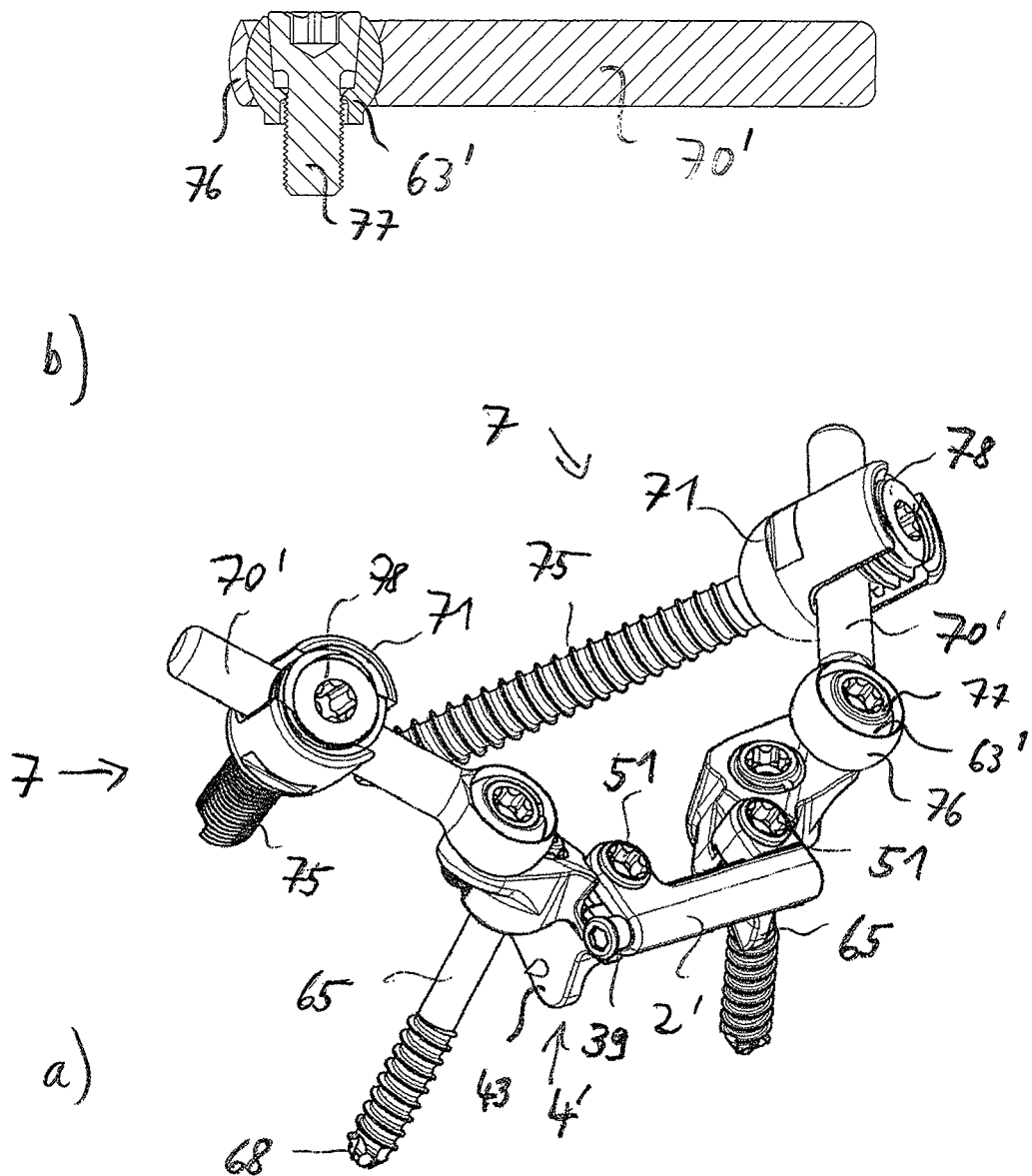
FIGS. 14a, b show a view of the top of the assembly and of the detail with the setting screws according to FIG. 13.

The fusion module 6 serves to fuse the lower facet joint of the vertebra 9 on which the implant is arranged with the upper facets of the vertebra 9 beneath it (see FIG. 14 in particular). To do so, the fusion module 6 has a main bearing on an upper facet 96 and a counterbearing on a lower facet 97 of the facet joint 98. The main bearing 60 is arranged on the end of the jaw elements 4 remote from the web. It comprises a receiving seat 61, which has an opening 62 with an interior designed in the form of a spherical cap. A fixation sleeve 63 whose outer jacket is designed to be spherical is arranged therein. It is thus held pivotably in the receiving seat 61. A transfacetal screw 65 having a head 66 on its proximal end and thread 67 in its distal end is inserted through the fixation sleeve 63. The length of the screw 65 is selected to correspond approximately to the thickness of the two facets 96, 97, which jointly form the facet joint 98. The screw 65 has a through-opening 68 along its central axis ("cannulated screw"). The pivotably movable support of the fixation sleeve 63 in the receiving seat 61 enables the screw 65 to be held in various axial orientations. In the exemplary embodiment shown here, the screw may be pivoted by an angle of ±15 degrees in all directions, based on the central axis of the opening 62. With an increased structural size, larger pivot angles are also possible, in particular up to 20 degrees or 25 degrees. The transfacetal screw 65 serves to be screwed in after insertion of the support module 1 and to form a counterbearing to the main bearing, which is formed on the fusion module 6, with its thread 67 engaging in the facet 97 of the neighboring vertebral body 9', so that on tightening of the screw, the facets 96, 97 are tightened against one another and the facet joint is immobilized. The transfacetal screw 65 may have a coating to promote bone growth on its shaft and/or threads 67.

The jaw elements 4, 4' are held on the holders 21, 31 so they are pivotably movable about the axis of the screws 50. An angle-limiting device is preferably provided to limit the angle range to a practical extent to thereby prevent an unwanted twisting of the jaw elements 4, 4', especially on insertion of the support module at its intended implantation site. In the exemplary embodiment shown here, this angle limiting device is formed by a radial protrusion 45, which is arranged in a rotationally fixed manner on the jaw element 4, 4' and is guided between the side walls of a recess 55 on the underside of the holders 21, 31. The side walls of the recess 55 act as stops here, which are limited in relation to the holders 21, 31. In the exemplary embodiment shown here, the dimensions of the recess 55 are selected to yield a pivot angle of 30° on the whole for each of the jaw elements 4, 4'.

Figure 1B:
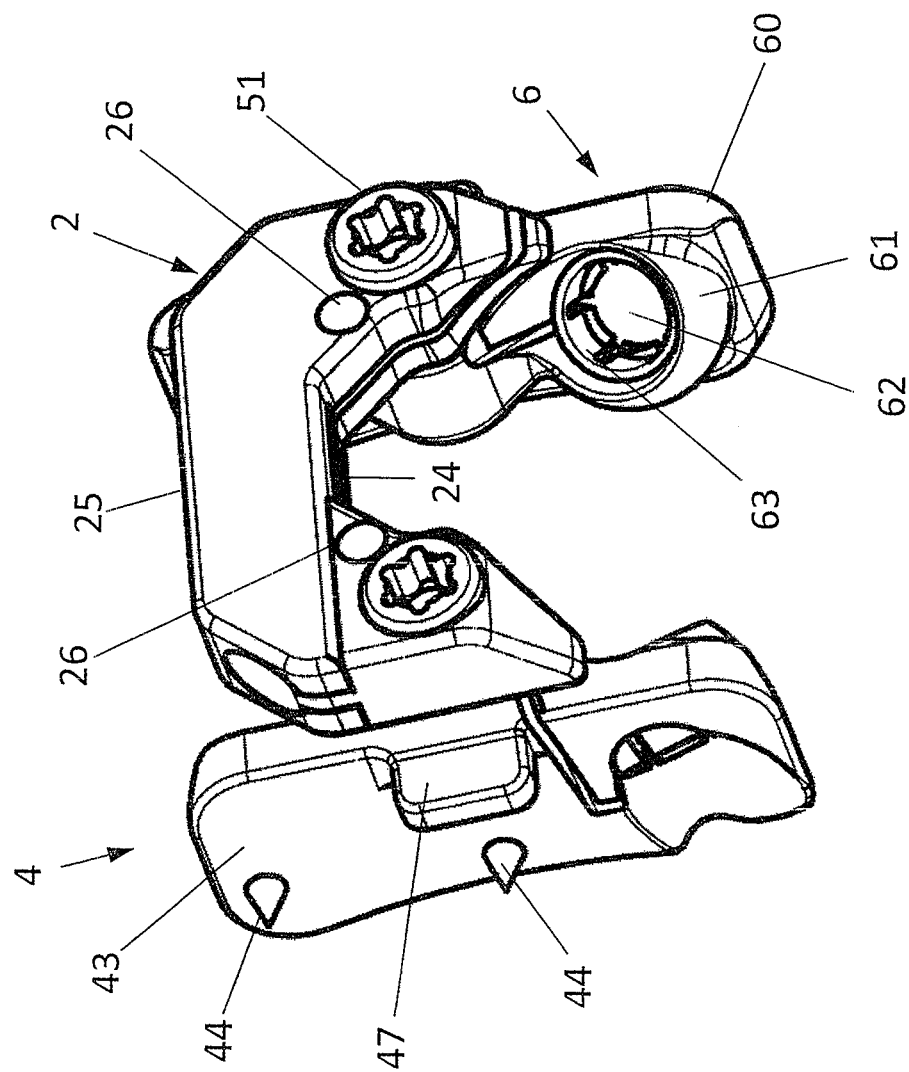
Figure 2A:
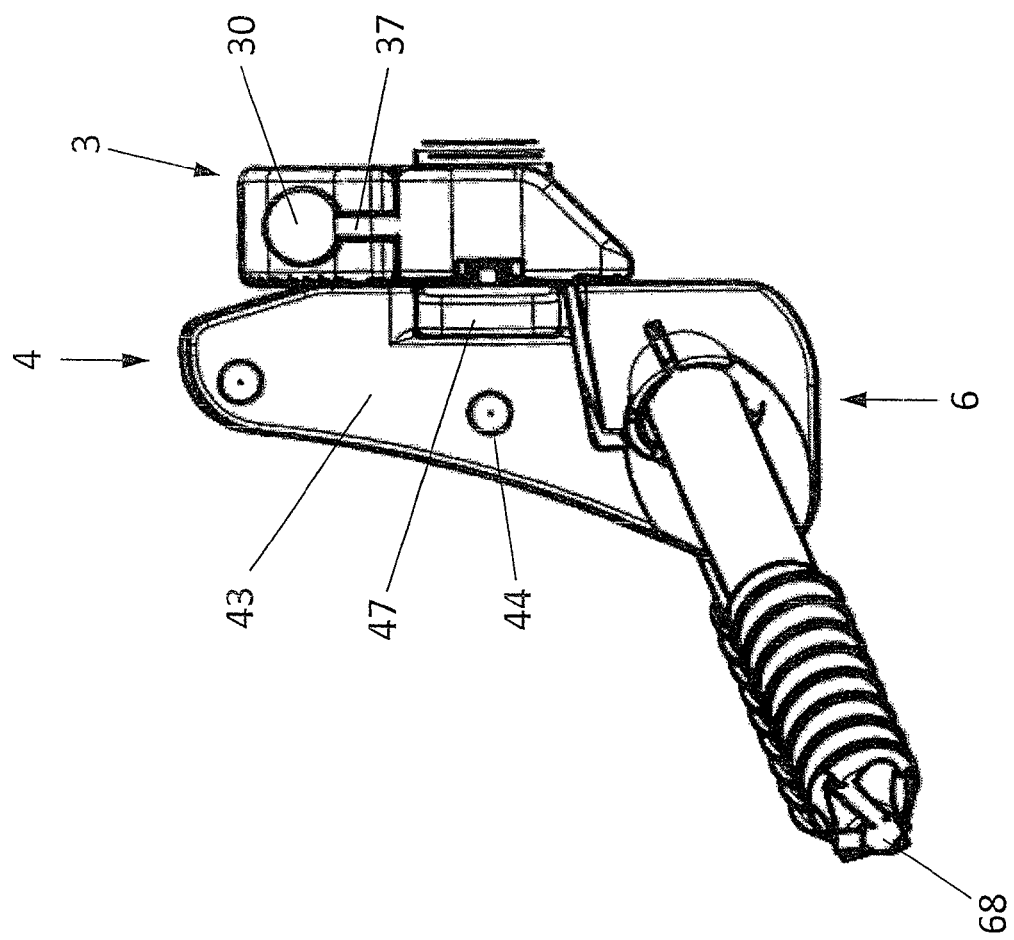
FIGS. 2a, b show a side view and a top view of the exemplary embodiment according to FIG. 1.
Figure 2B:
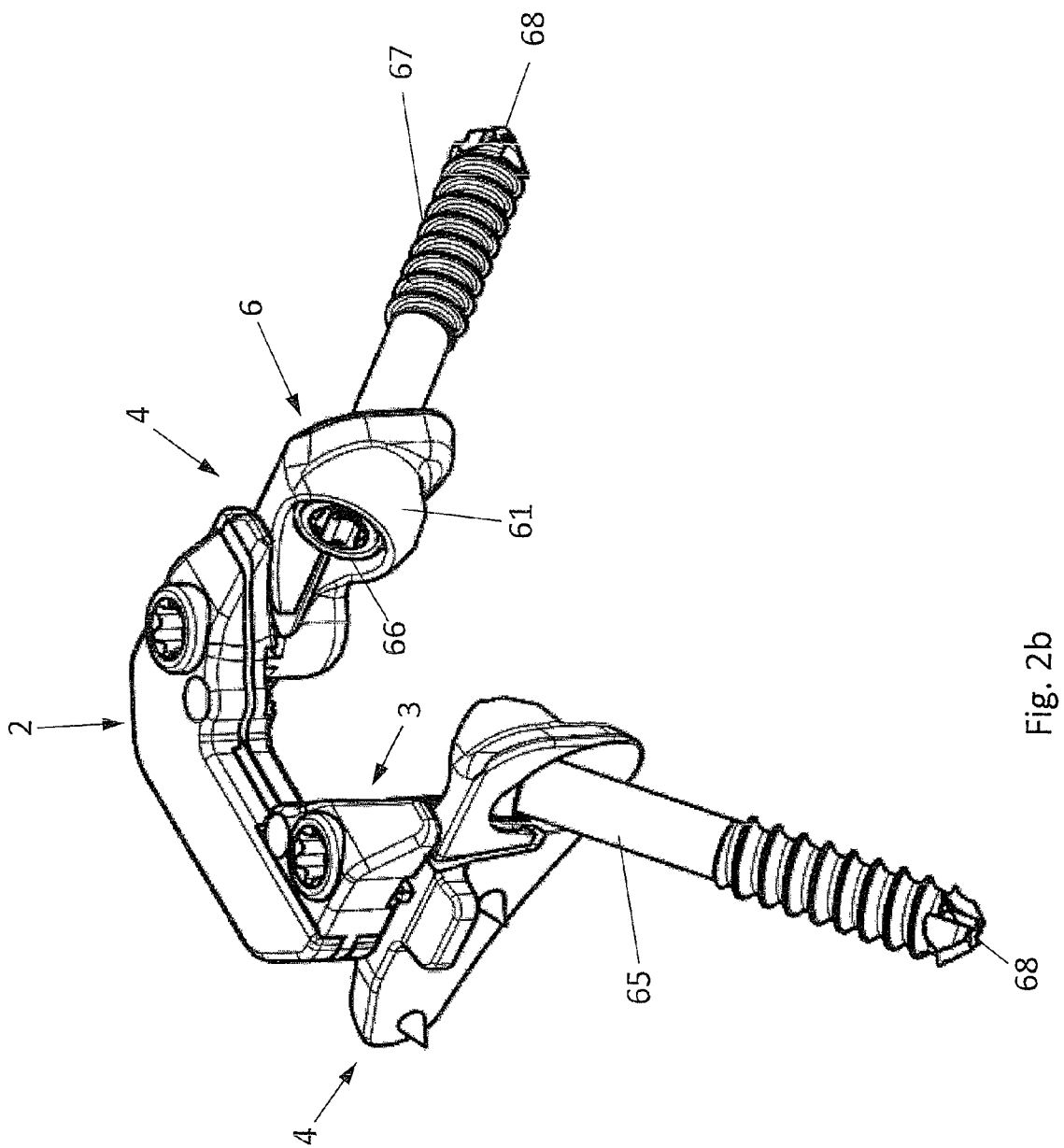
Figure 3:
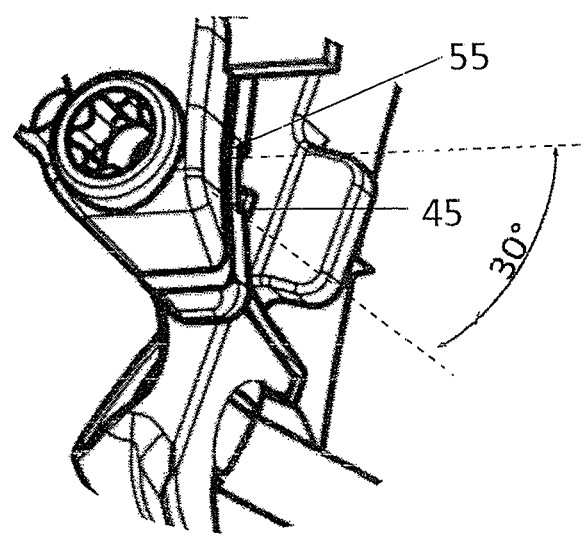
FIG. 3 shows a detailed enlargement of the exemplary embodiment shown in FIG. 1.
Figure 4A:
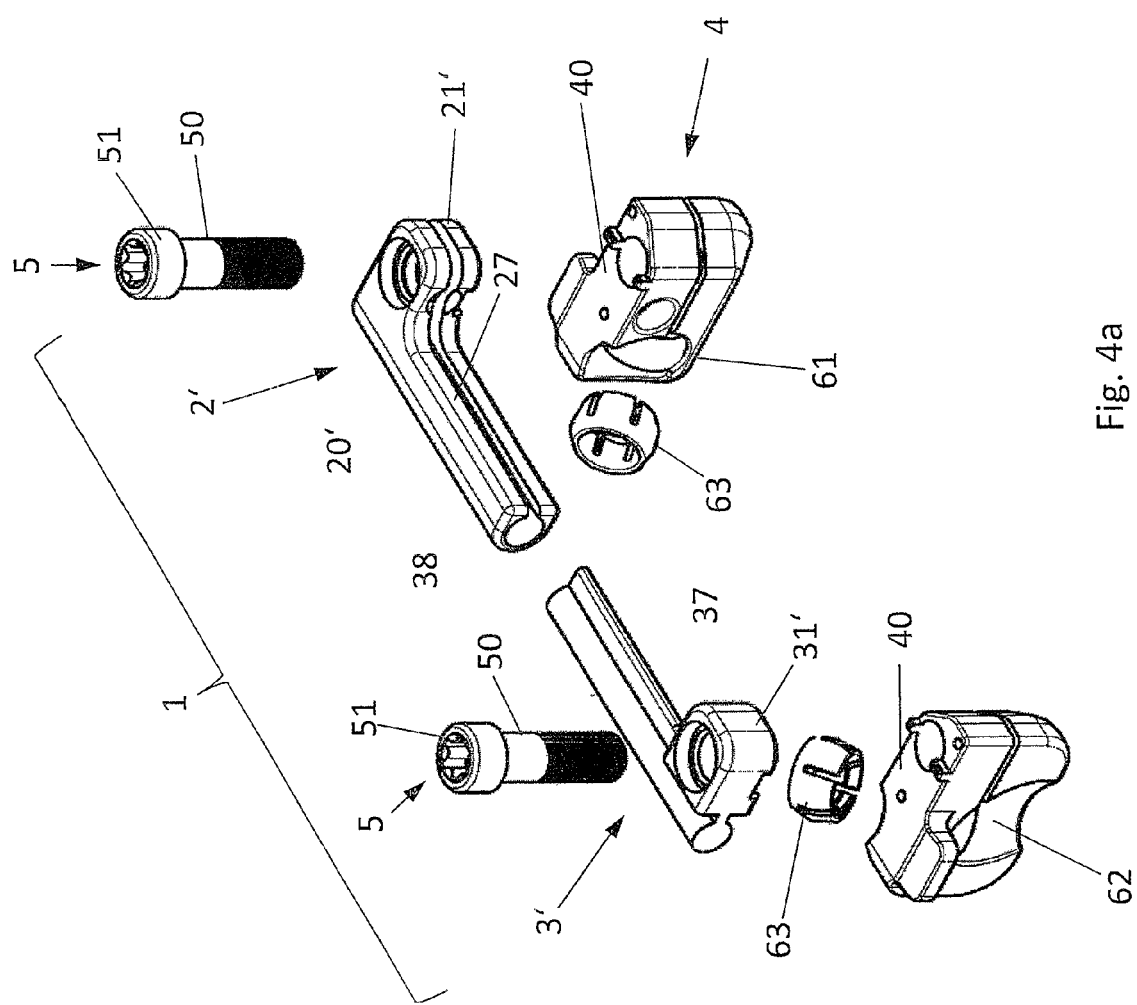
FIGS. 4a, b show a perspective view of the second exemplary embodiment in an assembled and a disassembled state.
Figure 4B:
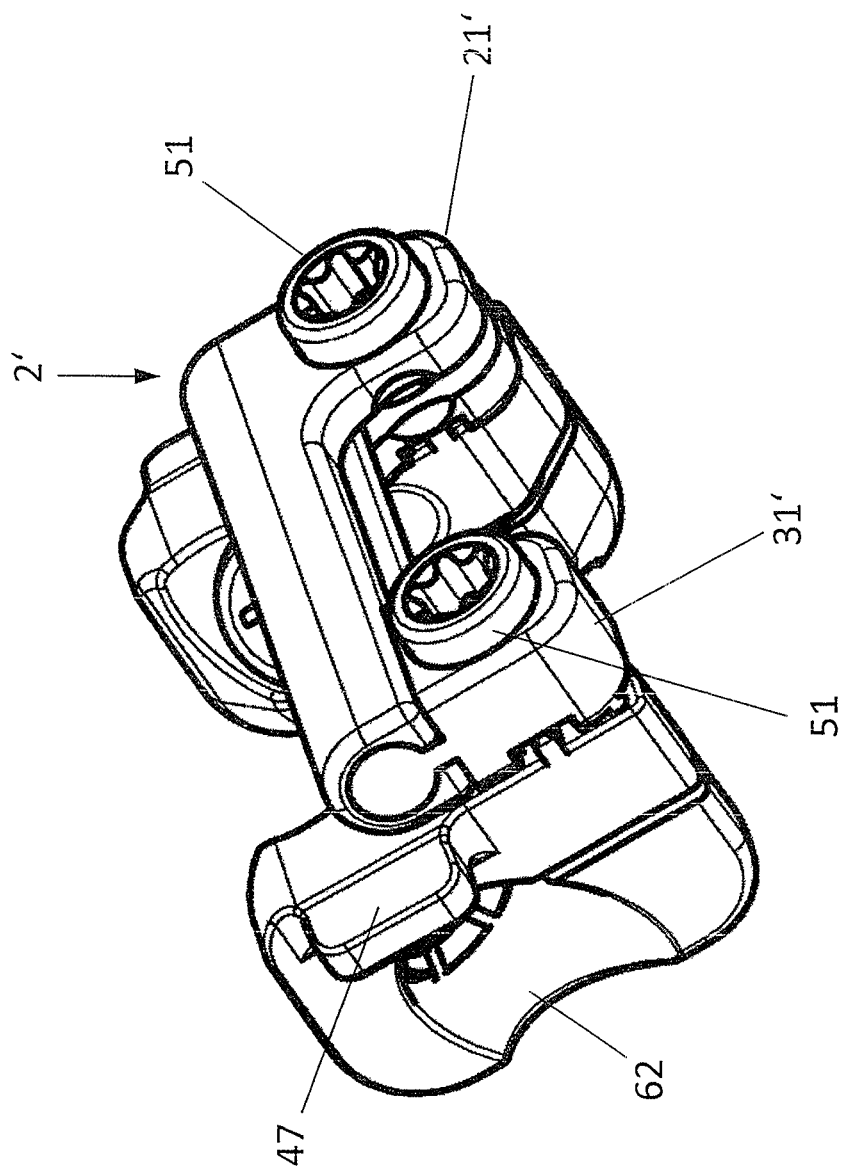

FIGS. 4a, b show a second exemplary embodiment which differs from the first exemplary embodiment according to FIGS. 1 to 3 essentially in that the support module has a much smaller structural height. The holders 21', 31' are designed to be more compact here than the holders 21, 31 in the first exemplary embodiment. In addition, the supporting web 20' does not have a rectangular cross section but instead has a square shape. Thus the support module 1' formed from the rail body 2' in the slide 3' requires a lower height in comparison with the support module 1 of the first exemplary embodiment. This allows implantation of the implant in a partial resection of the lamina. Therefore a lamina bridge may remain, so that, first of all, the natural stability of the vertebral body is largely preserved, and secondly the spinal protrusion on the vertebra extending downward can be preserved. This implantation is less invasive and is more conservative for the patient. In the second exemplary embodiment, as show in FIG. 4, the fusion module 6 is not arranged on the edge of the jaw elements 4 but instead is approximately at their center. This allows a smaller embodiment of the jaw elements 4. Moreover, the second exemplary embodiment is designed like the first exemplary embodiment so that reference may be made to the preceding discussion.

Figure 7:
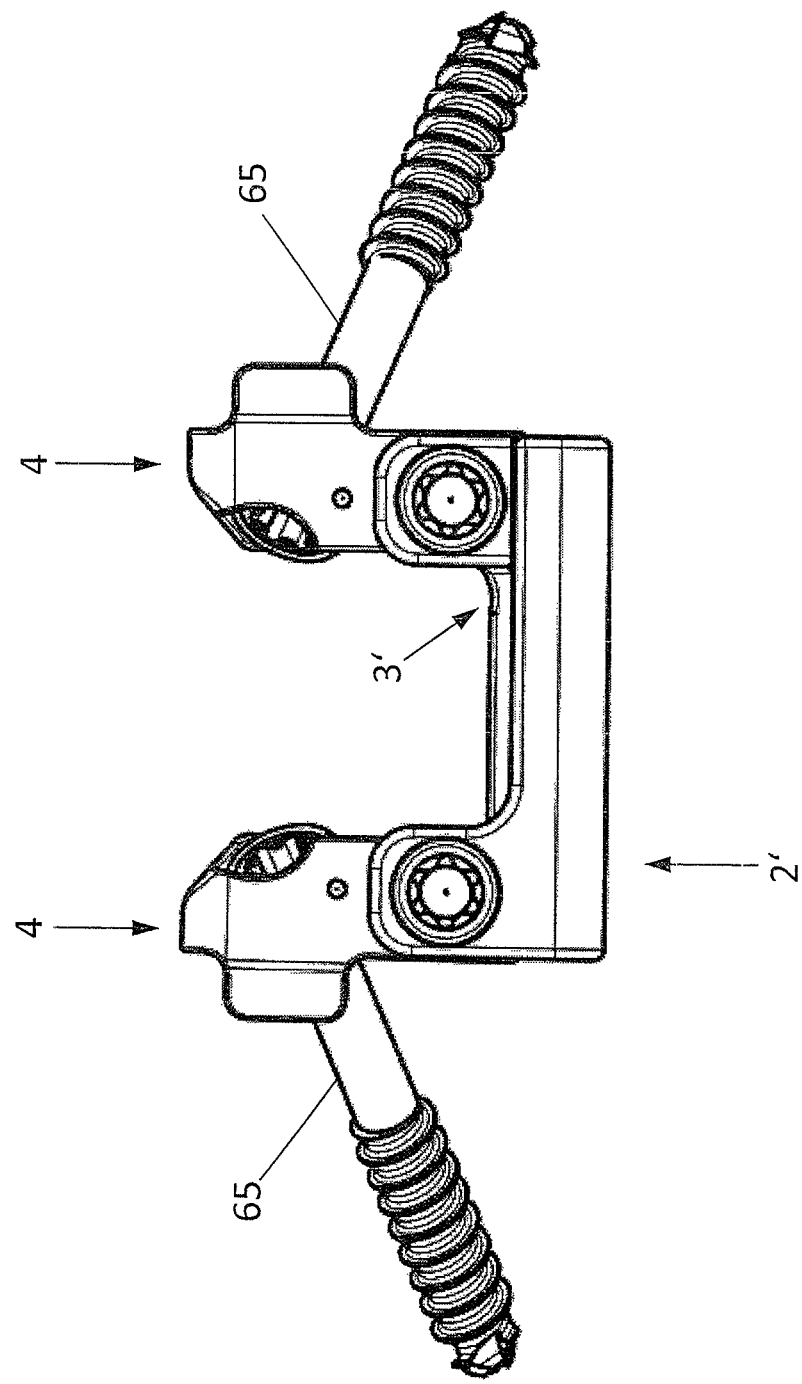
FIG. 7 shows a variant of the secondary exemplary embodiment.

FIG. 7 shows a variant of the second exemplary embodiment where the rail body 2' and the slide 3' are arranged in inverted positions on the jaw elements 4. The support module 1' therefore forms a definite U-shape, where the U is open at the top with respect to the implantation position. With the basic shape as illustrated in FIG. 4a, this is more like an H-shape or a U-shape that is open toward the bottom.

Figure 8:
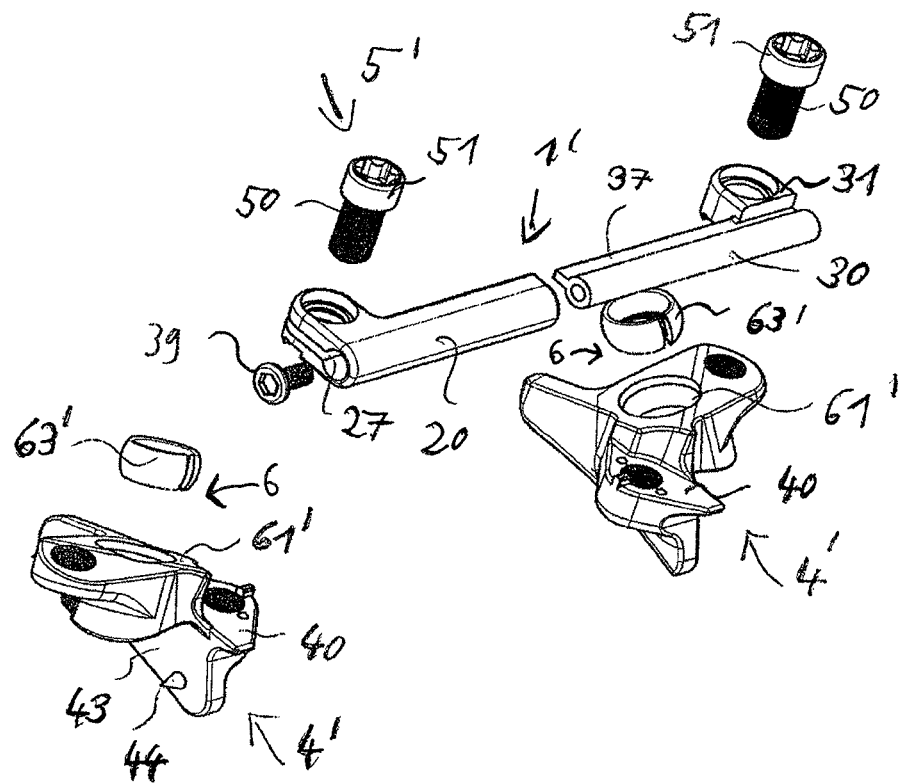
FIG. 8 shows an exploded view of a third exemplary embodiment.
Figure 9:
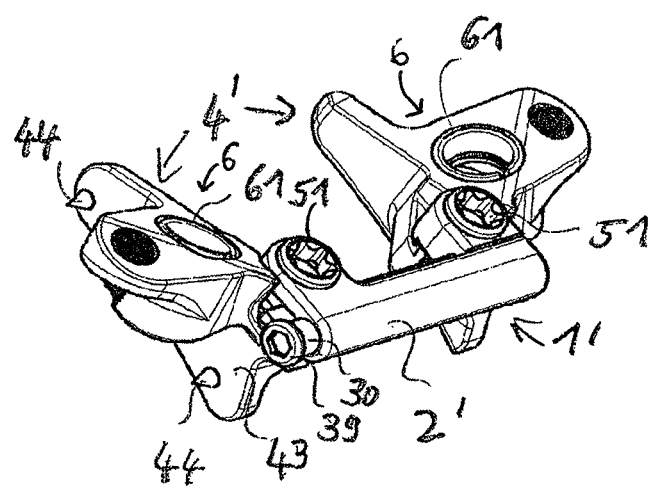
FIG. 9 shows a perspective view of the third exemplary embodiment in assembled form shown in FIG. 8.

A third exemplary embodiment is shown in FIGS. 8 and 9. It is based on the variant shown in FIG. 7 and, depending on the dimensioning, is suited both for the case of a partial resection of the lamina and for the case of the resection of the lamina over its entire height. Similar elements are illustrated with the same symbols as those of the second exemplary embodiment. As arranged in the variant shown in FIG. 7, the support module 1' is set inverse, that is, it forms an open U facing upward in an implant. The rod 30 is provided with a thread on its face side, in which a screw acting as a thickening element 39 has been set. Its head has a diameter large enough to prevent its passing through the slot 27. The jaw elements 4', which are held by a device 5, are provided with a receptacle seat 61', while an arrangement on the second exemplary embodiment on the support module 1 is selected, as will be described in more detail below.

Figure 5:
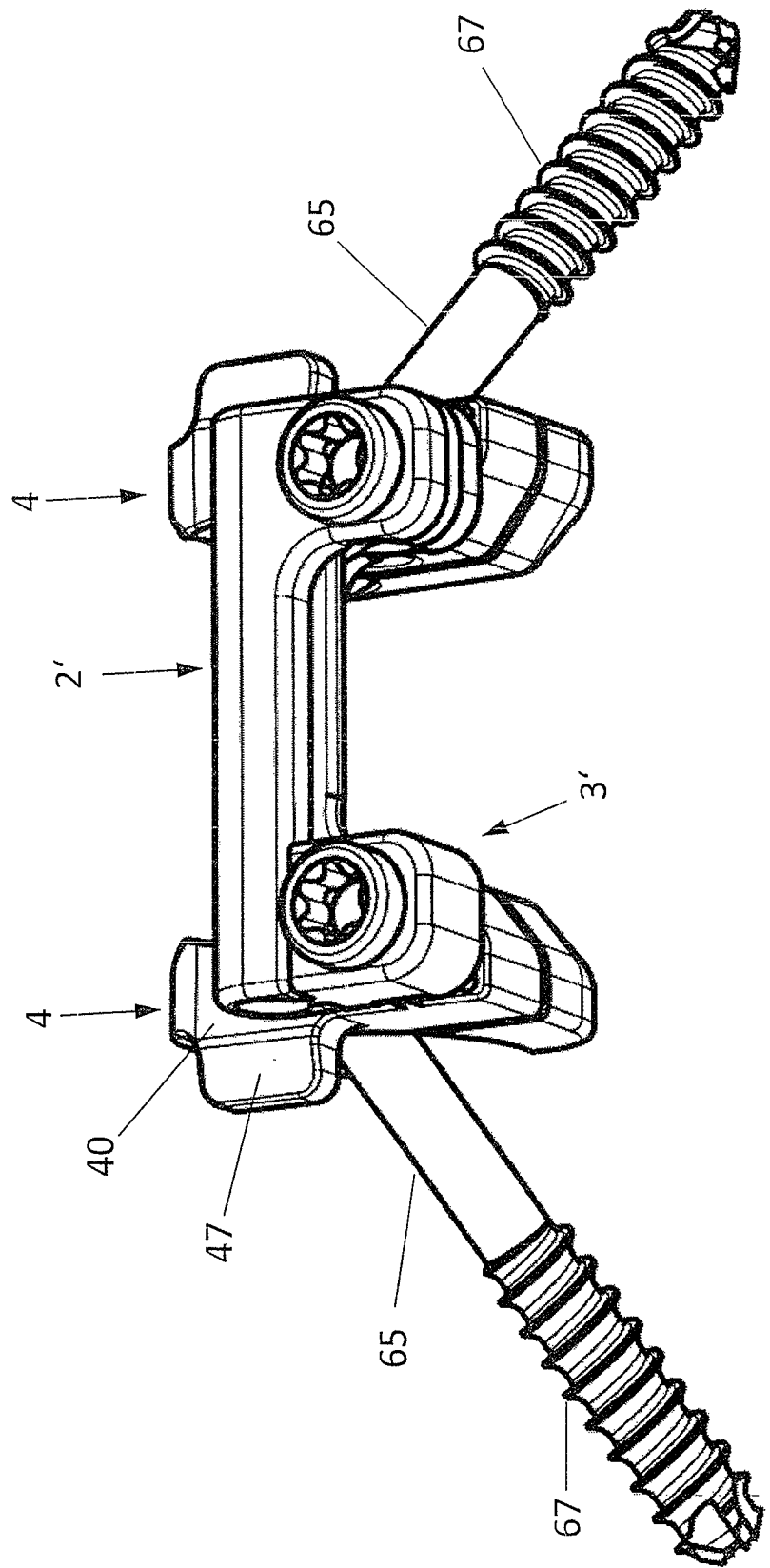
FIG. 5 shows a top view of this second exemplary embodiment shown in FIG. 4.
Figure 6:
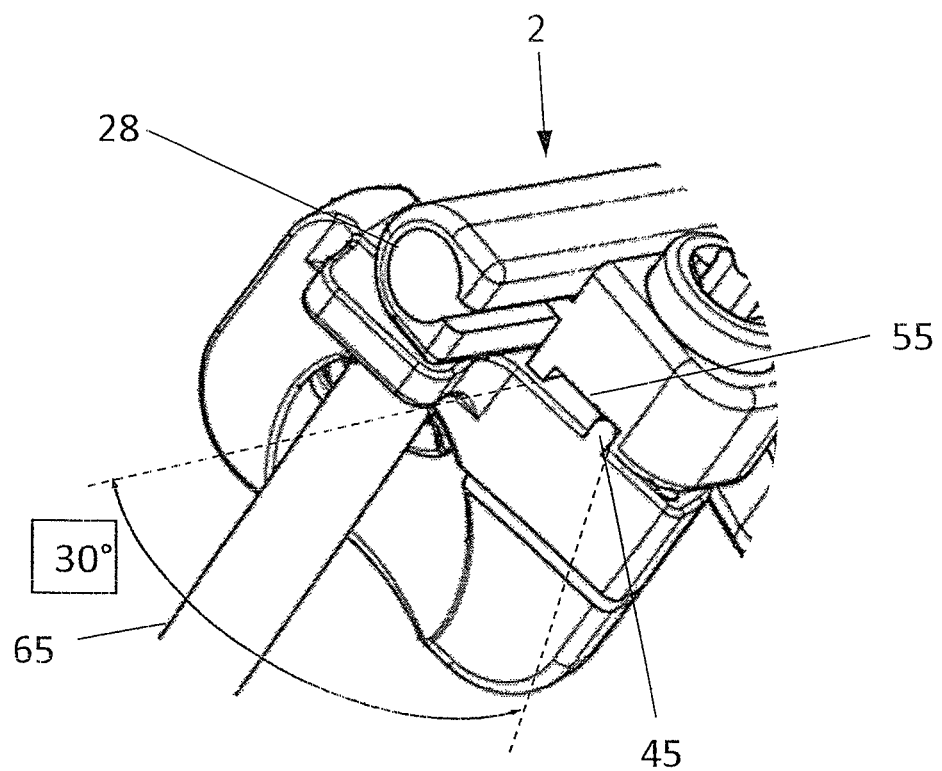
FIG. 6 shows a detailed enlargement of the second exemplary embodiment shown in FIG. 4.
Figure 10:
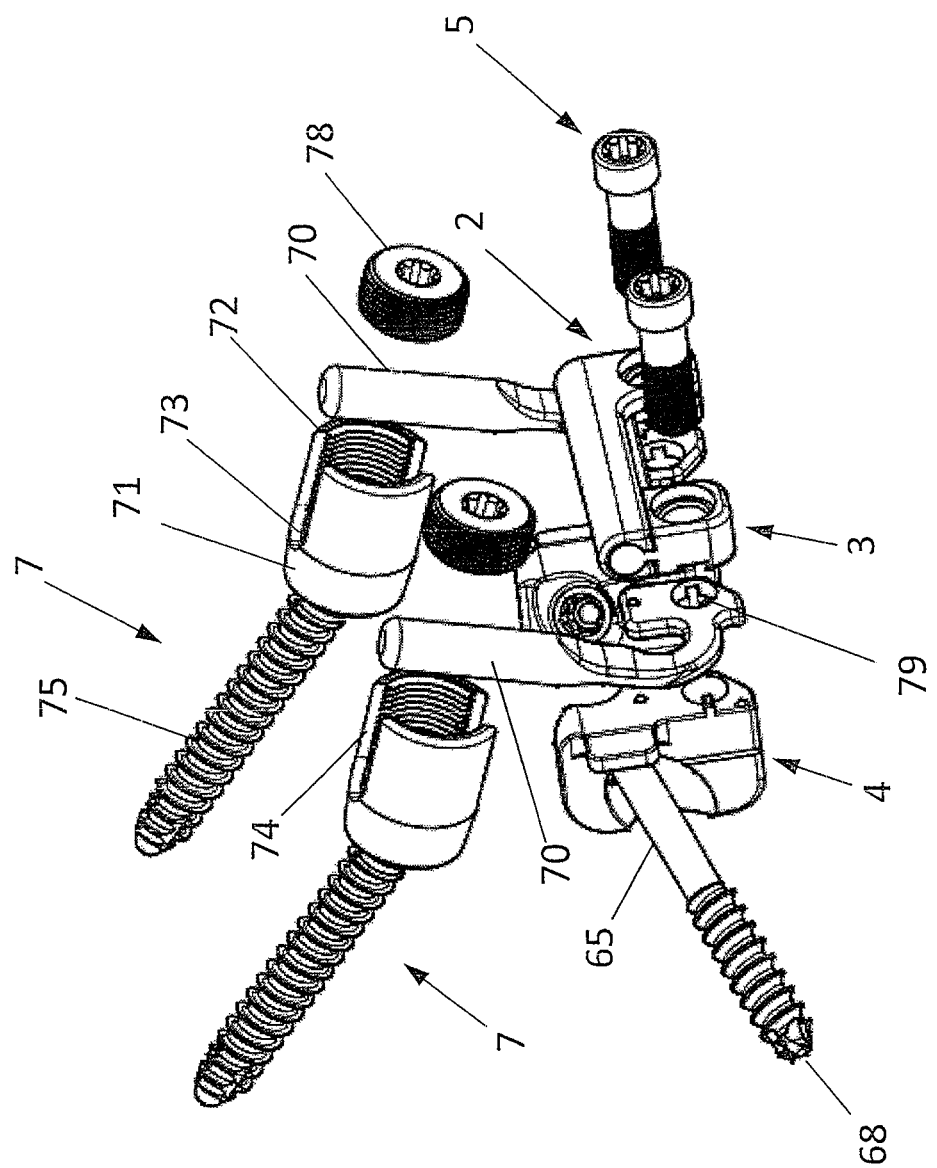
FIG. 10 shows an exploded view of the fourth exemplary embodiment.

A fourth exemplary embodiment is illustrated in FIG. 10. This is based on the second exemplary embodiment illustrated in FIGS. 4 to 6 and differs from that one essentially in that an additional pedicle support 7 has been provided. The pedicle support 7 represents an additional fastening option for the implant on the vertebral body. It increases the stability.

The pedicle support 7 comprises a pedicle screw 75 for each of the left and right pedicles 91 of the vertebral body 9. The structure is explained below with respect to the right pedicle screw 75. The corresponding description applies to the left pedicle screw 75. The pedicle support 7 is arranged over a supporting rod 70 on the support module 1. The supporting rod 70 has a plate-shaped protrusion on its lower end, with a through-opening 79 formed in it. The plate-shaped protrusion sits with its lower side on the top side of the jaw element 4 and with its top side of the lower side of the rail body 2. The screw 50 in the alignment device 5 is guided through the through-opening 79 in the protrusion. Thus in tightening the jaw element 4 on the rail body 2, the supporting rod 70 is also secured. On its opposite end the supporting rod 70 is designed to be circular.

A sleeve 71, a clamping cage 73 and a pressure element 78 are provided. The sleeve 71 is designed like a hollow cylinder with an opening 72 running from the posterior end to an anterior end. In its posterior area it has an inside thread and in its anterior it has a seating fit for the clamping cage 73 designed in the form of a spherical cap. The clamping cage 73 is designed like the fixation sleeve 63 and preferably has the same dimensions. The core diameter of the inside thread is selected so that the clamping cage 73 can be pushed through the inside thread to its seating fit. The sleeve 71 also has two diametrically opposed longitudinal slots 74, extending from the posterior end of the sleeve 71 over the entire range of the inside thread into the area of the seating fit of the through-opening 72. The clamping cage 73 is supported to be just as pivotable in its seating fit as the fixation sleeve 63 in the receiving seat 61 of the fusion module 6.

The pedicle screw 75 is inserted into the clamping cage 73 in such a way that it is held with its head in the clamping cage. The supporting rod 70 inserted into the slot 74 then presses on the head of the pedicle screw 75. Since the set screw 78 is screwed into the inside thread of the through-opening 72 until the set screw 78 comes to a stop against the supporting rod 70, the supporting rod 70 can be braced with respect to the head of the screw 75 and in turn via the clamping cage 73 by screwing it in so that the pedicle screw 75 is secured in its axial orientation in relation to the sleeve 71. This achieves a polyaxial bearing of the pedicle screw, namely in an angle range of ±15° about the central axis of the sleeve 71 (see FIG. 11b). The pivotable embodiment is not obligatory; it is also possible that the pedicle screw 75 is in a linear extension of the axis of the sleeve 71, as shown in FIG. 11a. By screwing the pedicle screw 75 into the pedicle 91 of the vertebra 9 and then bracing it by means of the set screw 78, an additional fastening effect can thus be achieved.

Figure 12A:
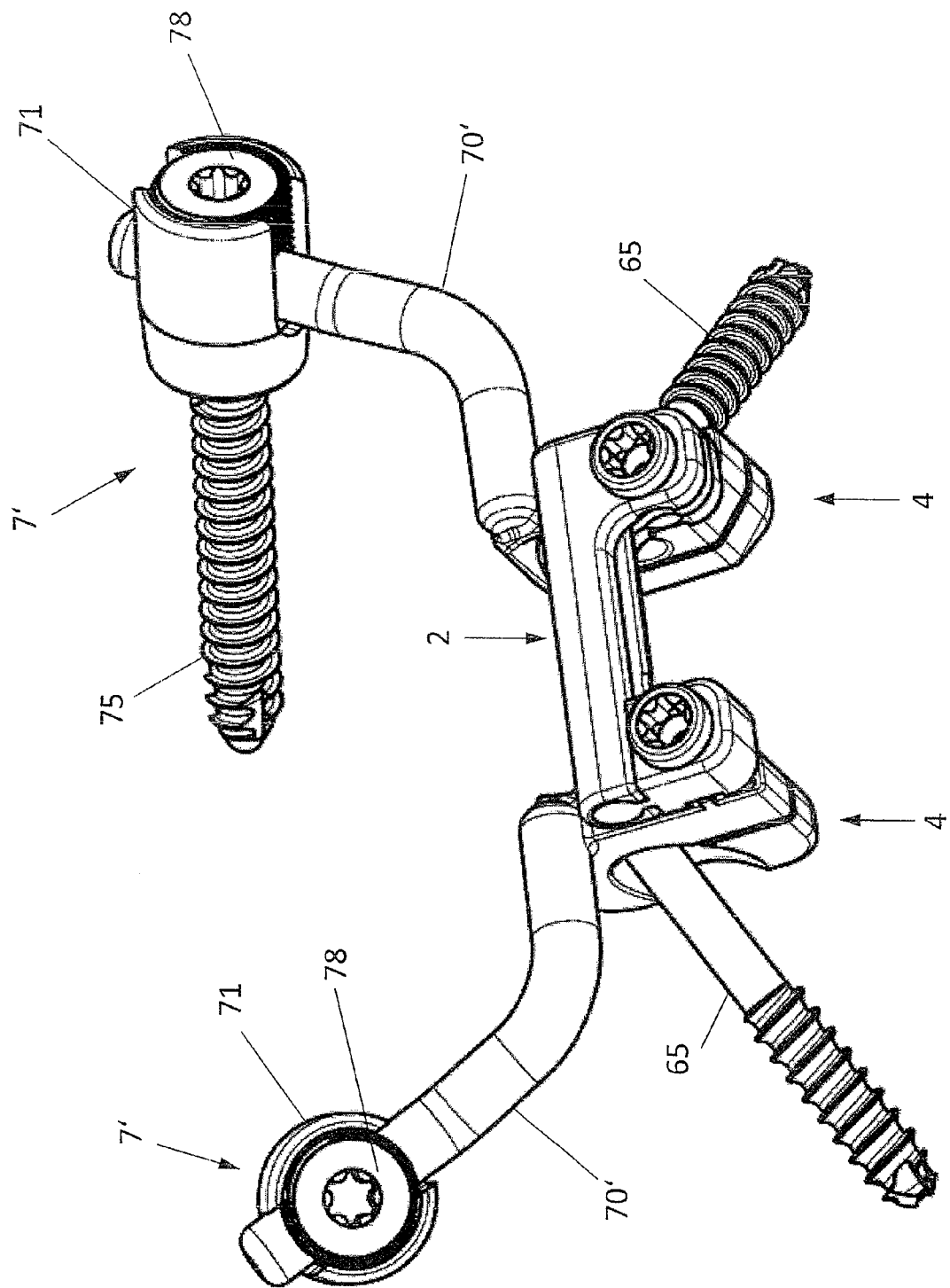
FIGS. 12a, b show variants of the fourth exemplary embodiment shown in FIG. 10.
Figure 12B:
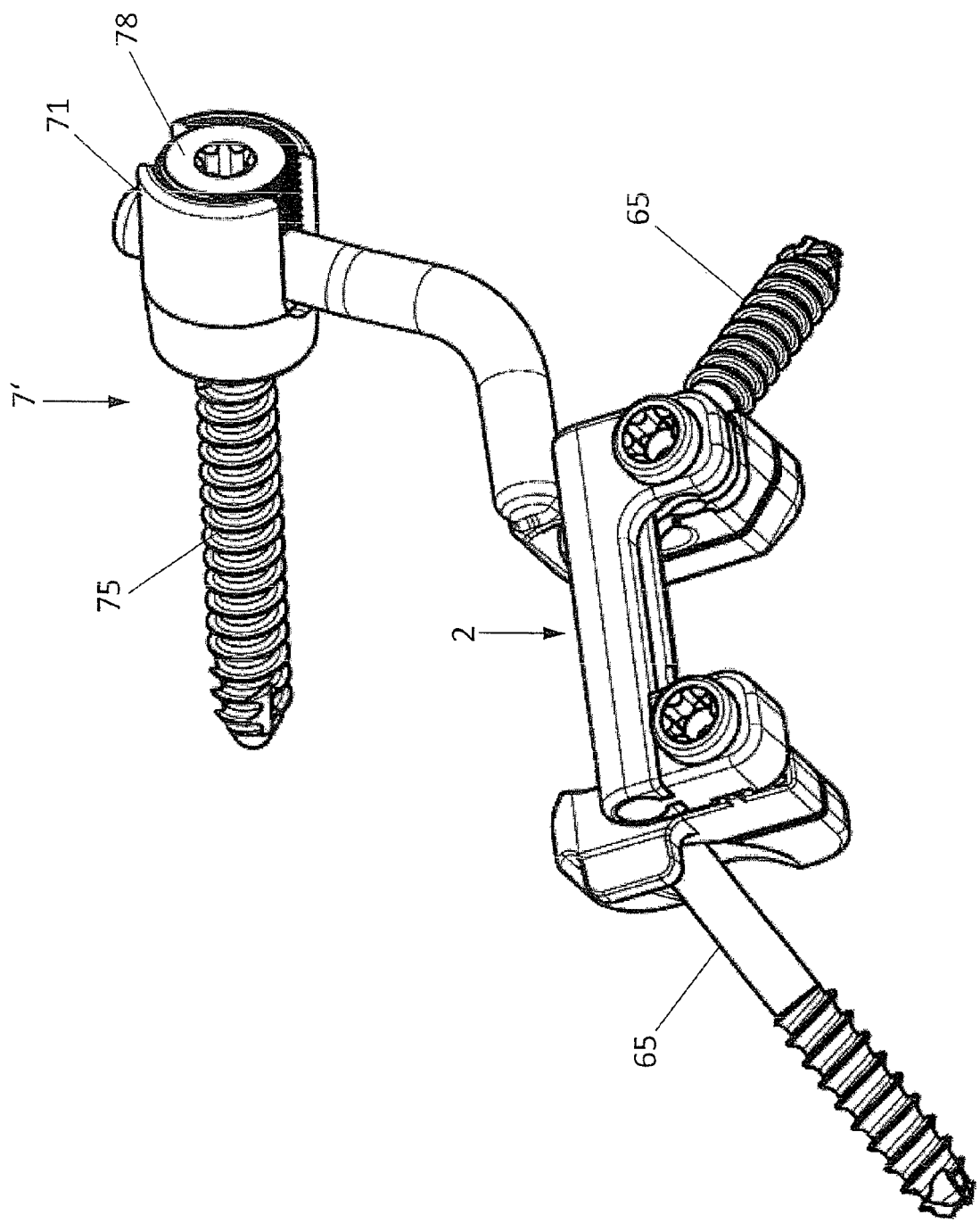

In one variant of the fourth exemplary embodiment, the supporting rod is designed with an arch and protrudes at a distance laterally (see FIG. 12a) Thus fixation a pedicle screw can also be achieved, but in contrast to the variant illustrated in FIG. 11a, b, this provides for a lateral orientation of the pedicle screw 75. The variant illustrated in FIGS. 11a, b, however, produces a medial orientation of the pedicle screws. The lateral orientation offers the advantage of creating a support on a broader basis, but it also has the substantial disadvantage that because of its protruding design, it leads to increased irritation of the surrounding tissue. It is not absolutely necessary for the lateral support to be provided on both sides. In additional variants, it is also possible to provide for the supporting rod to be designed in one piece with the jaw element and/or for the pedicle screw to be provided only on one side (see FIG. 12b).

Figure 13:
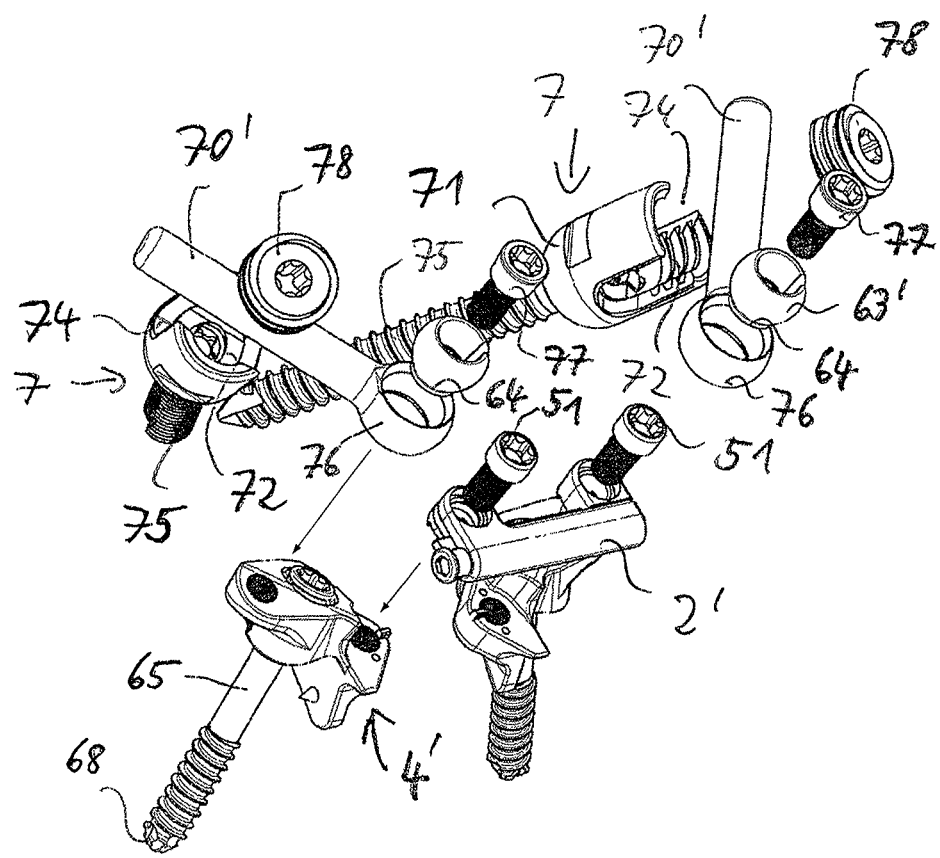
FIG. 13 shows an exploded view of the setting screws for the third exemplary embodiment shown in FIG. 8.

The exemplary embodiment shown in FIG. 13 involves a variant of the third exemplary embodiment, as shown in FIG. 8. It contrasts with the shorter jaw elements 4' shown in FIG. 8 and is also provided with a pedicle support 7' for additional fixation. The pedicle support 7' has a similar function and in essence is assembled similar to that which is shown in FIG. 8, where equivalent elements are provided with the same identification numbers. A significant difference lies in the fact that the bearing rod 70' is held on the jaw element 4' itself and not on the bearing body 1. For this, the jaw element is provided with an additional receptacle borehole, in which a separate locking screw 77 is set in with a cone-shaped head 77'. The bearing rod 70' is provided with an eye-shaped receptacle for secure fastening. A slotted bearing body 63' is set into this, which is made like the bearing body 63 and is provided with a pass-through opening. The locking screw 77 is inserted through the pass through opening and so forms a pivot bearing, which can be stopped by the action of the locking screw 77 that is set into the slotted bearing body 63'. For effective stopping, the bearing body 63' is provided with a radial member pointing to the inside, on which a short counter-thread (2 revolutions) is arranged for the locking screw 77. The radial member 69 divides the interior space of the bearing body 63' into a shorter cylindrical part 69" and a longer conical part 69'. The cone angle of the conical part 69' is complementary to the angle of the head 77' of the locking screw 77, In this way 2 things are accomplished. First, the thread of the locking screw 77 fits tightly into the counter-thread of the bearing body 63', and when screwed in, draws both components together; second, the cone shape causes a spreading of the bearing body 63', which once again leads to an increase of the fixation of the pivoting angle position of the bearing rod 70'. To achieve an unambiguous positioning within the eye 76, the bearing body 63' is provided with a circulating ring collar on one edge of the pass through opening. It is so sized that it fits into the receptacle borehole on the jaw element 4' and thus defines a normal position for the dome-shaped bearing body 63'. In this way the possible pivot angles for the pedicle support 7' are defined.

The instrument set provided for the implantation procedure is described below. It comprises a guide wire 80, a guide shaft 81, a tissue-protective tube 82, a cannulated screwdriver 83, another screwdriver 84, pincettes 85 and spreading forceps 87. The implantation in the case of a fusion implant according to the first exemplary embodiment is performed as described below. First by means of a suitable resection instrument (not shown) such as that which is known per se from the state of the art, a complete resection of the anterior portion of the lamina with the spinal protrusion is performed for the first exemplary embodiment. Thus two lateral laminar resection surfaces 94 are formed, creating between them a clearance which provides access to the channel. Now a decompression can be performed by an essentially known method. Once this has been performed, the implant according to the first exemplary embodiment is inserted. It is therefore placed in its location by means of the setting pincettes 85. This is done by inserting the receiving tips 86 of the setting pincettes 85 into receiving openings 26 on the top side of the support module 1. The receiving openings 26 may be separate openings, as illustrated in FIG. 1, or as shown in FIG. 2, they may be a combination with openings that are already present anyway for receiving a tool on the screw head 51 of the alignment device 5. The implant is accommodated on the setting pincettes 85 by frictional engagement.

The implant is guided to its intended implantation site in the clearance between the lamina resection surfaces 94 and is spread by spreading forceps 87. Therefore the slide 3 is removed from the rail body 2 in such a way that the jaw elements 4 are moved apart from one another until they are in contact at their outside surfaces 43 with the lamina resection surfaces 94. In doing so, the spreading forceps 87 are positioned before the setting pincettes 85 are removed. This is done in the manner illustrated in FIG. 12, namely by guiding the spreading forceps 87 from underneath. On their distal end, the spreading forceps 87 have gripping elements 89 which engage with a corresponding mating surface on the inside of the jaw elements 4. The gripping elements 89 may be designed in particular as gripping balls 89' which engage in a form-fitting manner in gripping troughs 29 (see FIG. 9) on the inside of the jaw elements 4. Once the spreading forceps 87' have been brought into engagement with the jaw elements 4 as shown in FIG. 12, the spread position of the spreading forceps can be secured by means of the ratchet 88'. The setting pincettes 87 can then be removed. The implant is held in its location under the influence of the spreading forceps 87'. The spreading forceps 87' are shaped so that they are angled in the cephalad direction, so that even in the attached state, there is access to the fusion module 6 and in particular the transfacetal screw 65 to be inserted there. Thus a primary positioning has been achieved.

For setting the transfacetal screw 65 in the accurate position, the guide shaft 81 is inserted into the opening 62 in the fusion module 6 in the correct orientation. This may be accomplished with x-ray monitoring. If the guide shaft 81 is correctly positioned, the guide wire 80 is inserted through the shaft and moved through the facets 96, 97. Once the guide wire 80 has reached its position, the guide shaft 81 is replaced by a tissue-protective tube 82. The cannulated facet screw 65 is then threaded with its hollow bore 68 onto the guide wire 80 and guided with the help of the screwdriver 83, also cannulated, through the tissue-protective tube 82 to the fusion module 6 and screwed in. tightening of the screw the screwdriver 83 is enabled by means of the cannulation, so that the positioning is ensured by the guide wire 80. Once the screw 65 has been tightened, the screwdriver 83 can be removed and the guide wire 80 with the tissue-protective tube 82 removed. The same procedure is performed on the other side for the contralateral facet screw 65. After both facet screws 65 have been tightened, the alignment device 5, 5' can be operated by tightening the locking screws 50 using the screwdriver 84 and thus the spread position of the support module 1 can be secured. The spreading forceps 87' can then be removed. The implant is secured in its location.

Figure 17A:
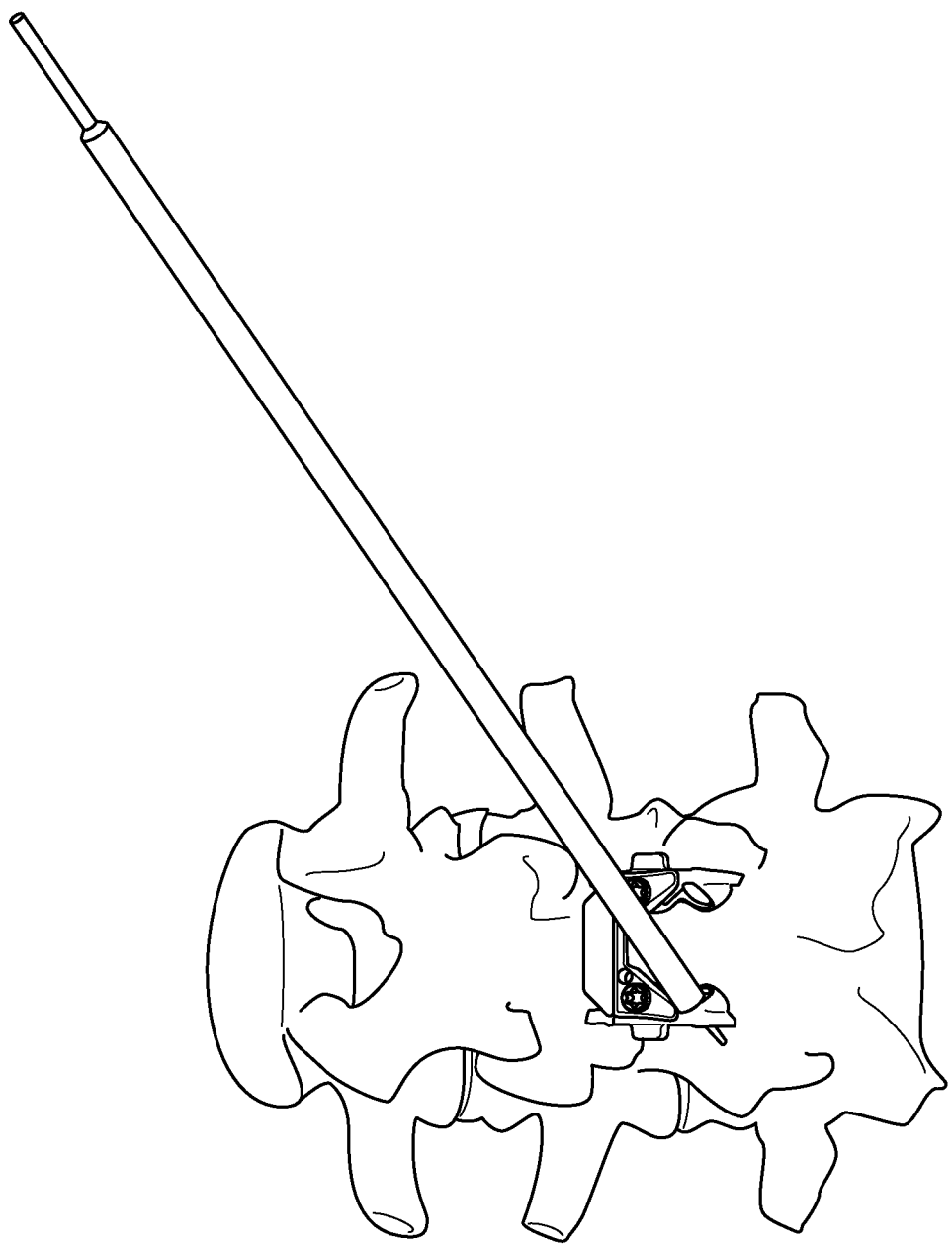
FIGS. 17a-d show illustrations of operating steps in implantation.
Figure 17B:
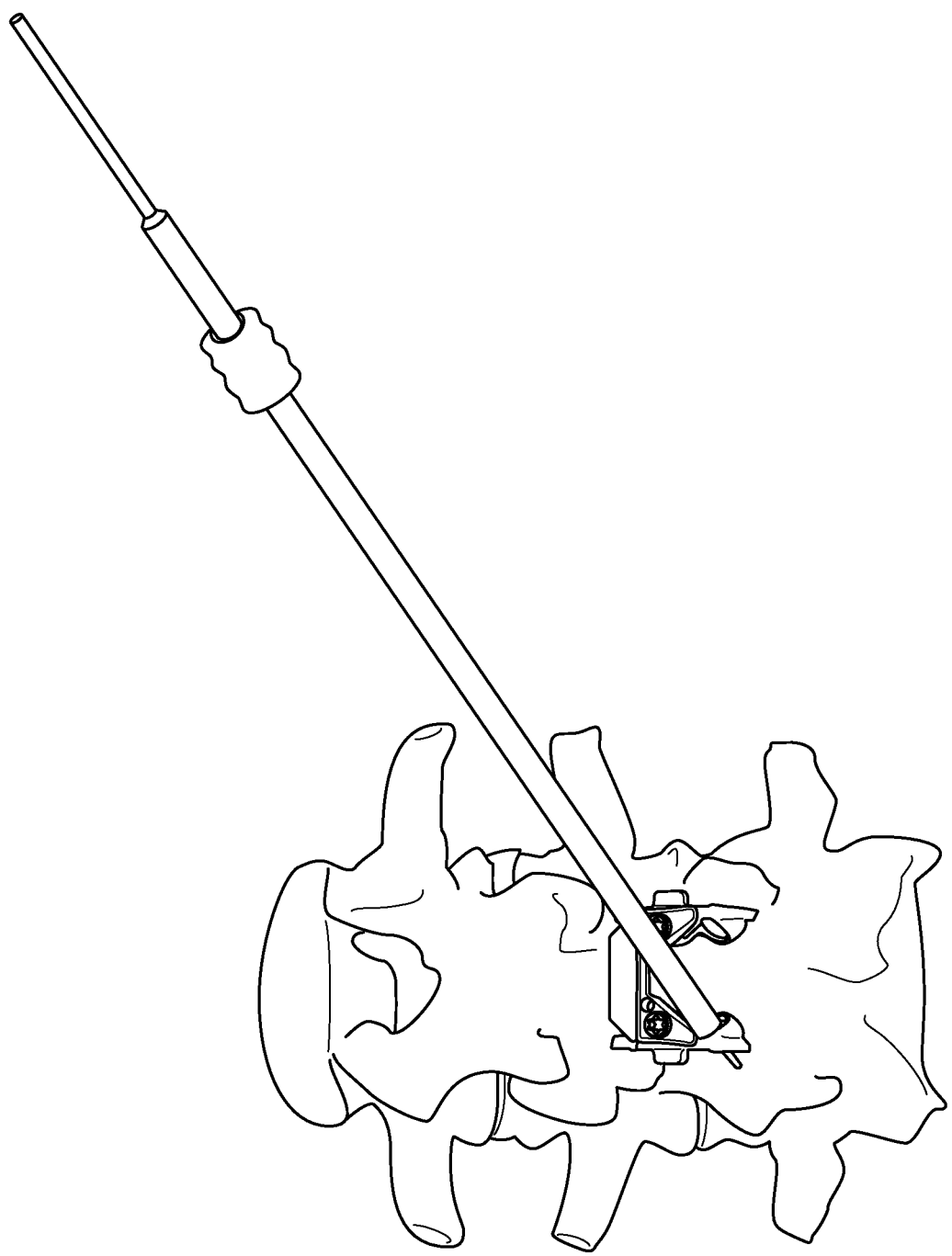
Figure 17C:
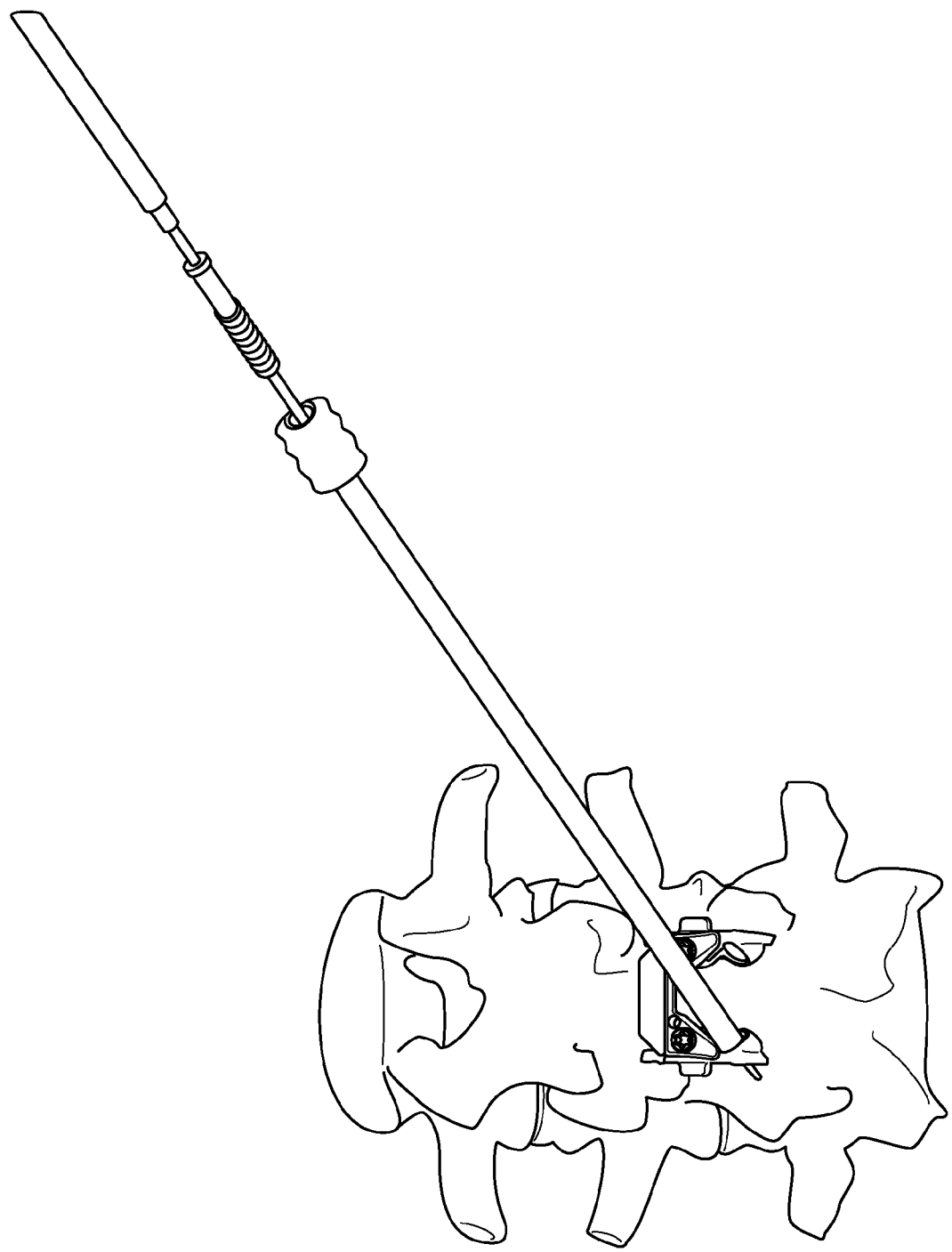
Figure 17D:
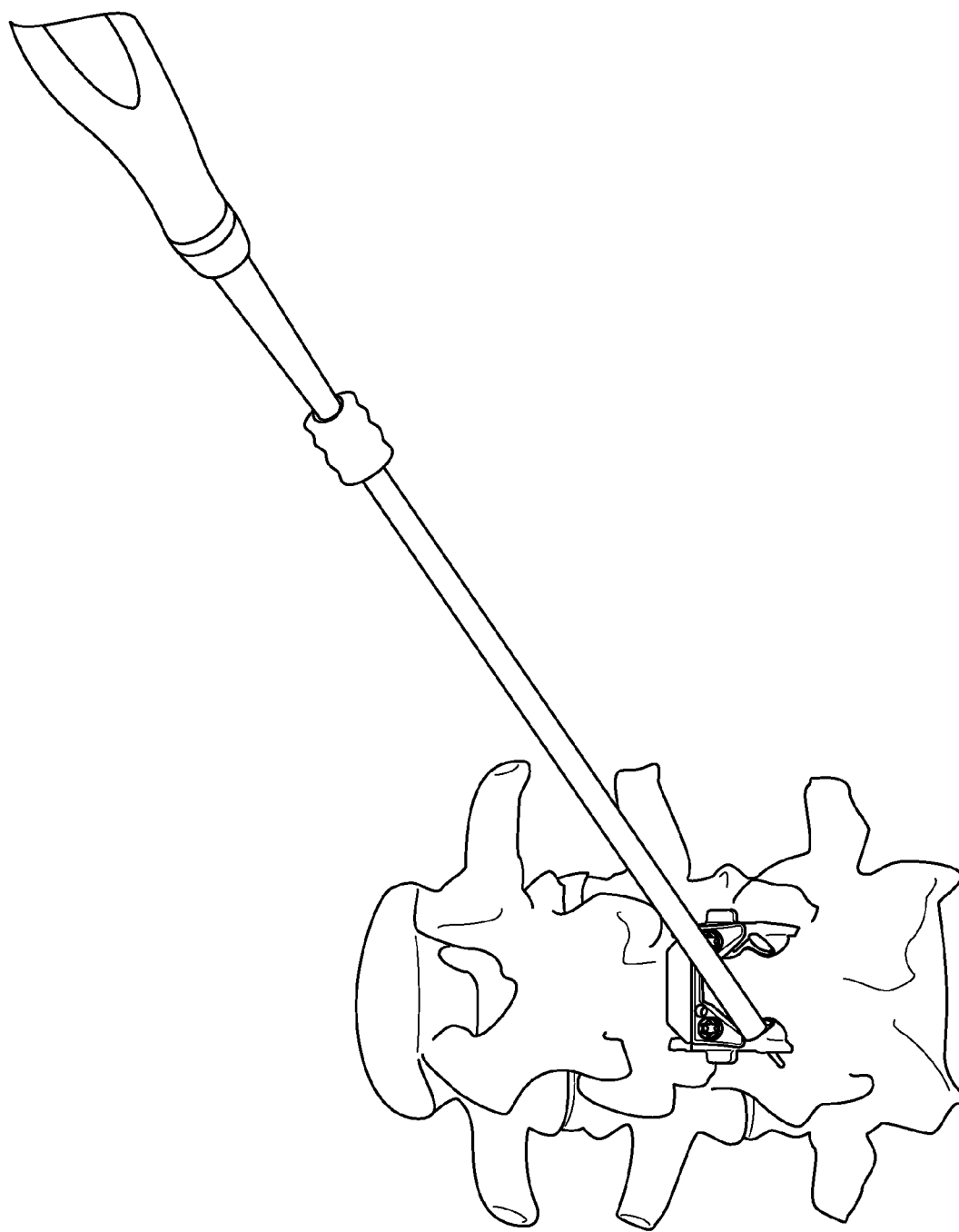
Figure 18A:
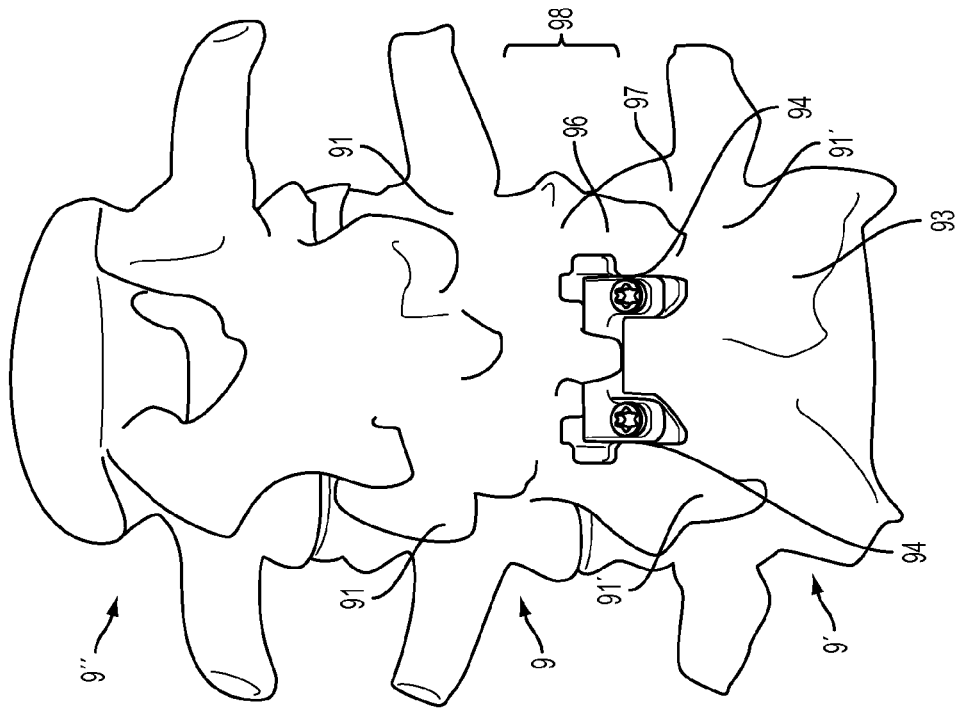
FIGS. 18a-c show illustrations of implants according to the exemplary embodiments in the implanted state.
Figure 18B:
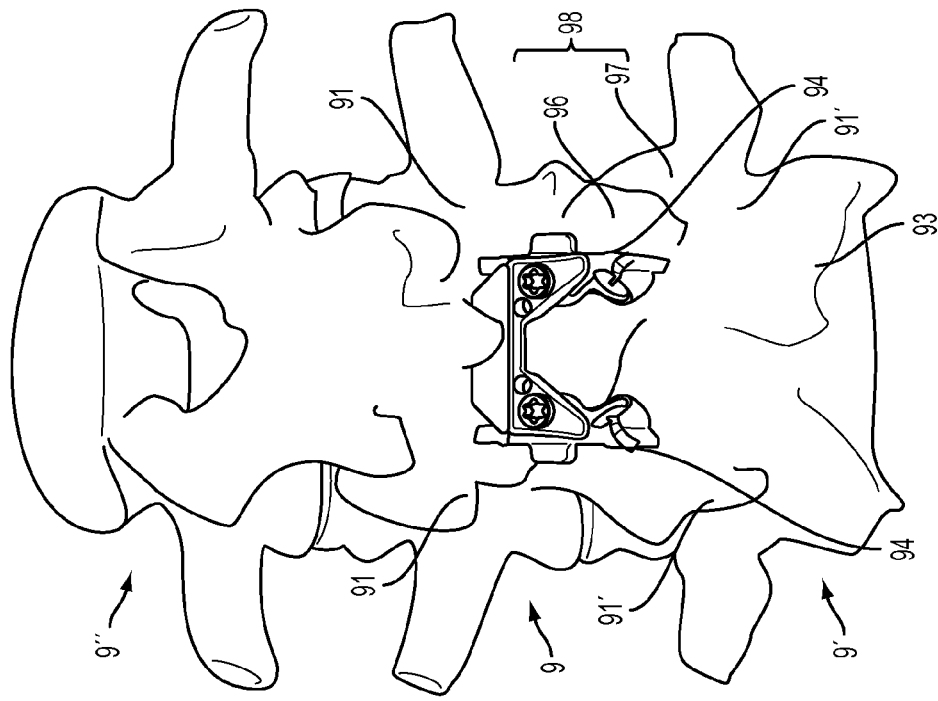
Figure 18C:
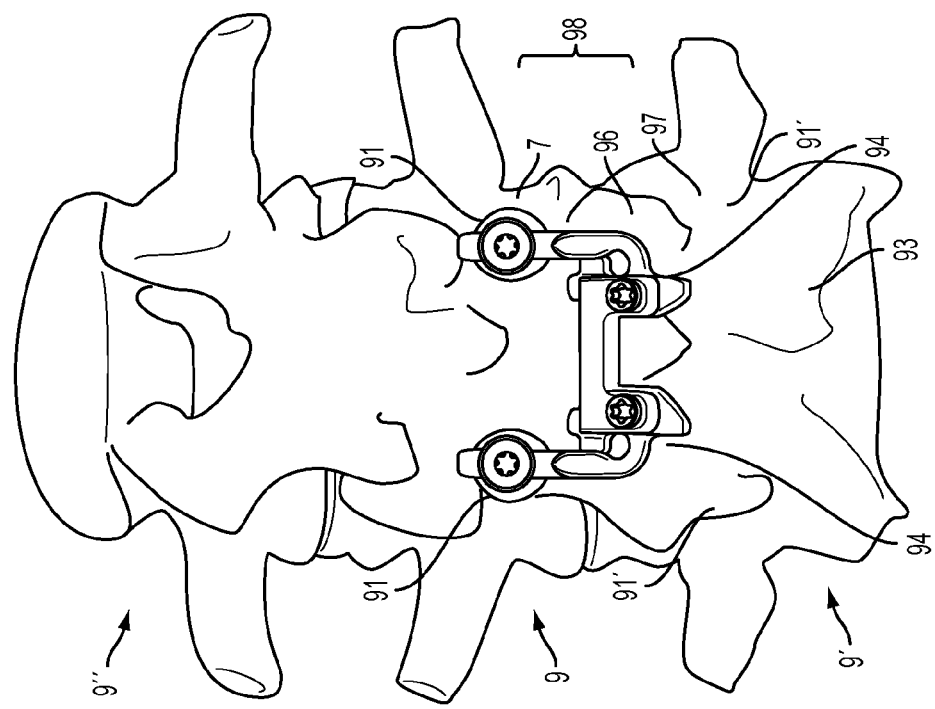

The installation position thereby achieved is shown in FIG. 18a for the implant according to the first exemplary embodiment. It can be seen here that the implant completely replaces the lamina of the vertebra 9. The second exemplary embodiment in the implanted state is shown in FIG. 17b. This implant has a smaller structural height and thus allows the lamina to be partially preserved, namely in the upper area with the spinal protrusion. This conservative variant is illustrated in FIG. 18b. Implantation of the third exemplary embodiment using the pedicle screws according to FIG. 10 is shown in FIG. 18c.

The invention claimed is:

1. A fusion implant for a facet joint of a vertebra, comprising:
　a support module;
　a first fusion module;
　a second fusion module, wherein the first fusion module and the second fusion module are arranged on the support module and each fusion module comprises a transfacetal fastener and an aperture for positioning the transfacetal fastener such that the transfacetal fastener can be installed through a facet joint portion of the vertebra into a corresponding facet joint portion of a neighboring vertebra, and
　wherein the support module is configured to permanently replace at least a part of a lamina arch of the vertebra and comprises
　　an expansion element,
　　jaw elements, wherein each jaw element has a contact surface for a laminar resection surface on an outer side facing away from the other jaw element and wherein each jaw element is arranged on a guide so at least one jaw element is longitudinally displaceable relative to the other jaw element, such that a distance between the fusion modules is variable via the expansion element, and
　　wherein the expansion element and the guide are configured to permanently replace the at least a part of the lamina arch of the vertebra.

2. The fusion implant of claim 1, further comprising a pedicle support arranged on the support module.

3. The fusion implant of claim 2, wherein the pedicle support has a bearing for pedicle screws.

4. The fusion implant of claim 3, wherein the pedicle screws have parallel axes, which lie across the guide.

5. The fusion implant of claim 3, wherein the pedicle support has a polyaxial support for pedicle screws.

6. The fusion implant of claim 2, wherein the pedicle support is held via an alignment device.

7. The fusion implant of claim 2, wherein lateral dimensions of the pedicle support amount to a maximum of 1.5 times lateral dimensions of the support module.

8. The fusion implant of claim 2, wherein the pedicle support protrudes laterally, and an axis of pedicle screws is aligned and converging toward a center of the support module.

9. The fusion implant of claim 1, further comprising a pedicle support arranged on one of the jaw elements.

10. The fusion implant of claim 9, wherein each of the fusion modules comprises a pivot bearing having a dome-shaped bearing body with a pass-through opening.

11. The fusion implant of claim 10, wherein each of the fusion modules comprises a dome-shaped bearing body in its pass-through opening with at least one of a radial member pointing inward and a circular ring collar on the edge of the pass-through opening.

12. The fusion implant of claim 10, wherein the dome-shaped bearing body is slotted.

13. The fusion implant of claim 9, wherein the pedicle support is arranged on one of the jaw elements with a pivot bearing.

14. The fusion implant of claim 1, wherein the fusion modules each have a main bearing configured to bear on an upper facet.

15. The fusion implant of claim 14, wherein the main bearing is pivotable.

16. The fusion implant of claim 15, wherein the main bearing comprises a fixation sleeve held pivotably in a spherical cap-shaped receiving seat.

17. The fusion implant of claim 14, wherein the fusion modules each have a mating configured to bear on another facet.

18. The fusion implant of claim 1, wherein the fusion modules are each arranged in a caudal area of the jaw elements.

19. The fusion implant of claim 18, further comprising a fusion module arranged on one of the jaw elements.

20. The fusion implant of claim 19, wherein the fusion module is arranged on one of the jaw elements in a support module side area.

21. The fusion implant of claim 1, wherein at least one of the jaw elements is provided with an alignment device for a variable orientation of the at least one jaw element in relation to the support module.

22. The fusion implant of claim 21, further comprising a locking screw provided as a bearing for the alignment device.

23. The fusion implant of claim 21, wherein the alignment device has a twist-proof device for limiting an angle of twist to a predetermined level.

24. The fusion implant of claim 1, wherein the expansion element comprises a rod on a slide and a groove having a complimentary shape on a rail body.

25. The fusion implant of claim 24, wherein the rod and the groove are secured to prevent twisting via a strip which engages in a slot in a form-fitting manner.

26. The fusion implant of claim 24, further comprising a thickening part arranged on a free end of the rod.

27. The fusion implant of claim 1, wherein the transfacetal fastener is a screw.

28. The fusion implant of claim 27, further comprising a coaxial access pathway to the transfacetal screw, wherein the coaxial access pathway is free of the support module.

29. The fusion implant of claim 1, wherein the support module has a dimension in a cephalad-caudal direction, which amounts to less than half of the extent of a contact surface in the same direction.

30. The fusion implant of claim 29, wherein the fusion modules are each arranged in the central area of the jaw elements.

31. The fusion implant of claim 1, wherein the fusion modules are each arranged flexibly on the support module.

32. The fusion implant of claim 1, wherein the jaw elements have a narrower contact surface in a cephalad area than in a caudal area.

33. The fusion implant of claim 1, wherein one of the jaw elements is provided with an alignment device.

34. The fusion implant of claim 1, wherein the contact surfaces each comprise a stop surface having at least one of pointed protrusions and a coating which promotes bone growth.

35. A set comprising a fusion implant of claim 1, and an instrument set, wherein the instrument set comprises:
    an elongated guide wire,
    a guide shaft through which the guide wire can be inserted, having one end designed for being received on a main bearing of the fusion modules and
    a cannulated screwdriver.

36. The set of claim 35, wherein the instrument set further comprises:
    spreading forceps, and
    separate setting pincettes.

37. The set of claim 36, wherein the spreading forceps are angled in a cephalad direction in their working position and provide free access for the guide wire, and the separate setting pincettes are connected to the fusion implant via a friction-engaged connection.

38. A method for inserting a fusion implant of claim 1, comprising:
    resecting at least a portion of the lamina of a vertebra body;
    inserting the fusion implant into a space created by the resection;
    spreading the fusion implant;
    inserting a guide wire via one of the fusion modules into a facet joint to be fused;
    pushing the transfacetal fastener onto the guide wire and inserting it into the one of the fusion modules;
    tightening the transfacetal fastener; and
    tightening the expansion element.

39. The method of claim 38, wherein a cannulated screwdriver is used for tightening the transfacetal fastener.

40. The method of claim 38, wherein transfacetal fastener comprises a cannulated screw.

* * * * *